United States Patent
Liu et al.

(10) Patent No.: US 8,852,257 B2
(45) Date of Patent: *Oct. 7, 2014

(54) SHEATHS USED WITH POLYMER SCAFFOLD

(75) Inventors: Annie P. Liu, Cupertino, CA (US); Jason Phillips, Lake Elsinore, CA (US); Mark C. Johnson, Murrieta, CA (US); Brenna Hearn Lord, San Francisco, CA (US); Jeremy Beer, Mountain View, CA (US); Travis Yribarren, Campbell, CA (US); Steve Saville, Temecula, CA (US); Marc L. Speck, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 306 days.

This patent is subject to a terminal disclaimer.

(21) Appl. No.: 13/165,662

(22) Filed: Jun. 21, 2011

(65) Prior Publication Data
US 2012/0324696 A1 Dec. 27, 2012

(51) Int. Cl.
| | |
|---|---|
| *A61F 2/84* | (2006.01) |
| *A61F 2/958* | (2013.01) |
| *A61F 2/97* | (2013.01) |
| *A61F 2/82* | (2013.01) |
| *A61F 2/95* | (2013.01) |
| *A61M 25/10* | (2013.01) |

(52) U.S. Cl.
CPC . *A61F 2/958* (2013.01); *A61F 2/82* (2013.01); *A61F 2002/9522* (2013.01); *A61F 2/97* (2013.01); *A61M 2025/1081* (2013.01)
USPC .......................................... 623/1.11; 623/1.12

(58) Field of Classification Search
USPC ........................ 623/1.11, 1.12; 606/108, 200; 604/103.05, 160, 161
See application file for complete search history.

(56) References Cited

U.S. PATENT DOCUMENTS

| | | | |
|---|---|---|---|
| 4,243,050 | A | 1/1981 | Littleford |
| 4,581,025 | A | 4/1986 | Timmermans |
| 4,710,181 | A | 12/1987 | Fuqua |
| 5,015,231 | A | 5/1991 | Keith et al. |
| 5,158,545 | A | 10/1992 | Trudell et al. |
| 5,211,654 | A | 5/1993 | Kaltenbach |
| 5,250,033 | A | 10/1993 | Evans et al. |
| 5,352,236 | A | 10/1994 | Jung et al. |
| 5,458,615 | A | 10/1995 | Klemm et al. |
| 5,545,211 | A | 8/1996 | An et al. |
| 5,569,294 | A | 10/1996 | Parkola |
| 5,591,226 | A | 1/1997 | Trerotola et al. |

(Continued)

OTHER PUBLICATIONS

U.S. Appl. No. 12/861,719, filed Aug. 23, 2010, Wang et al.

(Continued)

*Primary Examiner* — Ryan Severson
*Assistant Examiner* — Anh Dang
(74) *Attorney, Agent, or Firm* — Squire Patton Boggs (US) LLP

(57) ABSTRACT

A medical device includes a polymer scaffold crimped to a catheter having an expansion balloon. A sheath pair is placed over the crimped scaffold after crimping to reduce recoil of the crimped polymer scaffold and maintain scaffold-balloon engagement relied on to hold the scaffold to the balloon when the scaffold is being delivered to a target in a body. The sheath pair is removed by a health professional before placing the scaffold within the body.

6 Claims, 13 Drawing Sheets

(56) References Cited

U.S. PATENT DOCUMENTS

| | | | |
|---|---|---|---|
| 5,647,857 A | 7/1997 | Anderson et al. | |
| 5,653,697 A | 8/1997 | Quiachon et al. | |
| 5,693,066 A | 12/1997 | Rupp et al. | |
| 5,709,703 A | 1/1998 | Lukic et al. | |
| 5,749,852 A | 5/1998 | Schwab et al. | |
| 5,765,682 A | 6/1998 | Bley et al. | |
| 5,776,141 A | 7/1998 | Klein et al. | |
| 5,782,855 A | 7/1998 | Lau et al. | |
| 5,817,100 A | 10/1998 | Igaki | |
| 5,868,707 A | 2/1999 | Williams et al. | |
| 5,893,868 A | 4/1999 | Holman et al. | |
| 5,964,730 A | 10/1999 | Williams et al. | |
| 6,010,529 A | 1/2000 | Herweck et al. | |
| 6,110,146 A | 8/2000 | Berthiaume et al. | |
| 6,132,450 A | 10/2000 | Hanson et al. | |
| 6,152,944 A | 11/2000 | Holman et al. | |
| 6,197,016 B1 | 3/2001 | Fourkas et al. | |
| 6,254,609 B1 | 7/2001 | Vrba et al. | |
| 6,334,867 B1 | 1/2002 | Anson | |
| 6,342,066 B1 | 1/2002 | Toro et al. | |
| 6,355,013 B1 | 3/2002 | Van Muiden | |
| 6,416,529 B1 | 7/2002 | Holman et al. | |
| 6,447,540 B1 * | 9/2002 | Fontaine et al. | 623/1.12 |
| 6,533,806 B1 | 3/2003 | Sullivan et al. | |
| 6,783,542 B2 | 8/2004 | Eidenschink | |
| 6,790,224 B2 | 9/2004 | Gerberding | |
| 6,805,703 B2 | 10/2004 | McMorrow | |
| 6,827,731 B2 | 12/2004 | Armstrong et al. | |
| 6,899,727 B2 | 5/2005 | Armstrong et al. | |
| 7,198,636 B2 | 4/2007 | Cully et al. | |
| 7,314,481 B2 | 1/2008 | Karpiel | |
| 7,347,868 B2 | 3/2008 | Burnett et al. | |
| 7,384,426 B2 | 6/2008 | Wallace et al. | |
| 7,618,398 B2 | 11/2009 | Holman et al. | |
| 2002/0052640 A1 | 5/2002 | Bigus et al. | |
| 2003/0004561 A1 | 1/2003 | Bigus et al. | |
| 2003/0212373 A1 | 11/2003 | Hall et al. | |
| 2004/0073286 A1 | 4/2004 | Armstrong et al. | |
| 2004/0143315 A1 | 7/2004 | Bruunn et al. | |
| 2006/0015171 A1 | 1/2006 | Armstrong et al. | |
| 2008/0010947 A1 | 1/2008 | Huang et al. | |
| 2010/0004735 A1 | 1/2010 | Yang et al. | |

OTHER PUBLICATIONS

U.S. Appl. No. 12/916,349, filed Oct. 29, 2010, Papp.
U.S. Appl. No. 13/089,225, filed Apr. 18, 2011, Roberts et al.
U.S. Appl. No. 13/107,666, filed May 13, 2011, Wang.

* cited by examiner

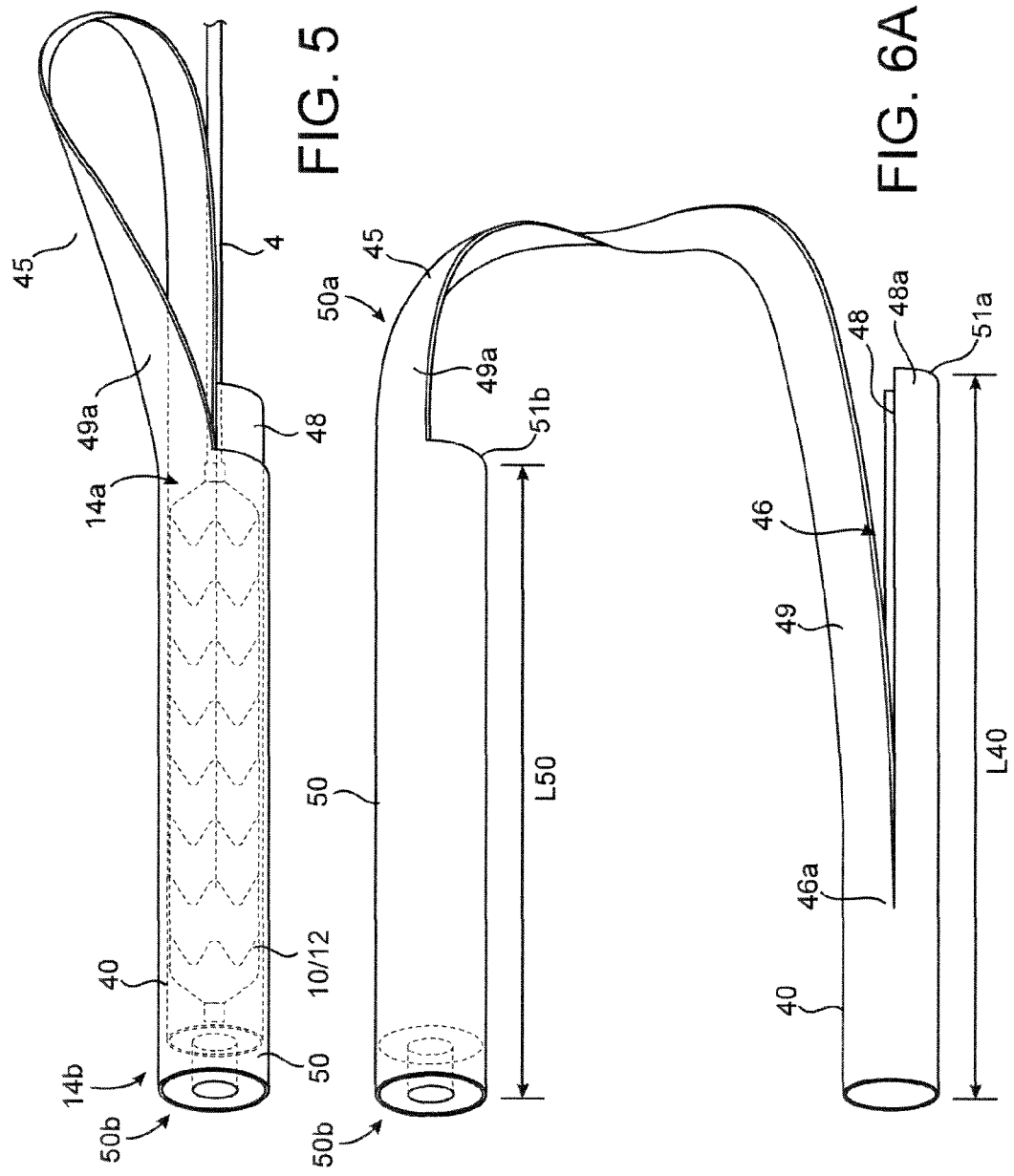

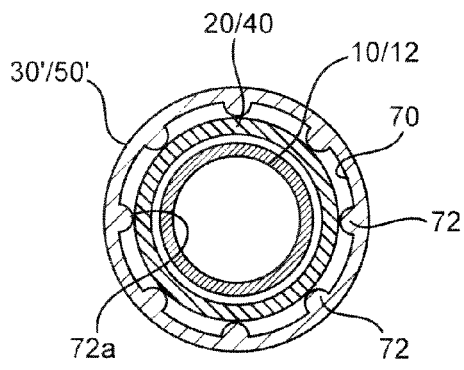
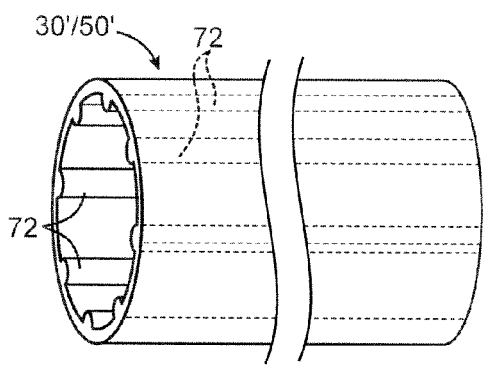
FIG. 7A    FIG. 7B
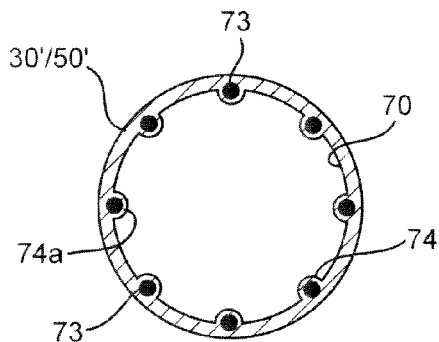
FIG. 7C
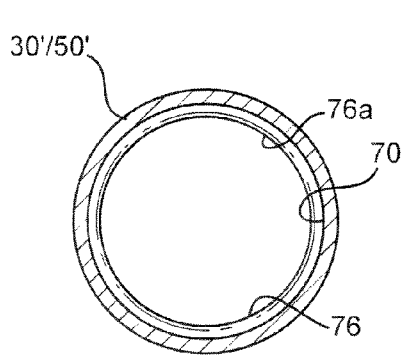
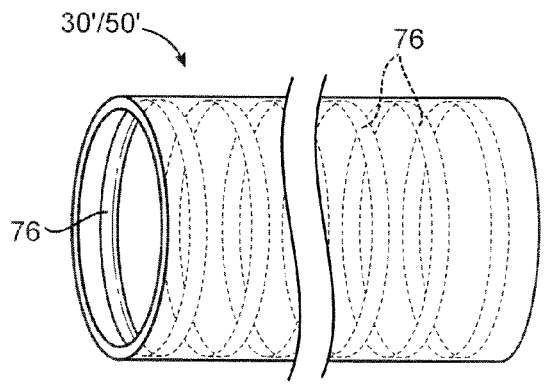
FIG. 8A    FIG. 8B

SHEATHS USED WITH POLYMER SCAFFOLD

FIELD OF THE INVENTION

The present invention relates to drug-eluting medical devices; more particularly, the invention relates to sheaths for polymeric scaffolds crimped to a delivery balloon.

BACKGROUND OF THE INVENTION

A variety of non-surgical interventional procedures have been developed over the years for opening stenosed or occluded blood vessels in a patient caused by the build up of plaque or other substances on the walls of the blood vessel. Such procedures usually involve the percutaneous introduction of an interventional device into the lumen of the artery. In one procedure the stenosis can be treated by placing an expandable interventional device such as an expandable stent into the stenosed region to hold open and sometimes expand the segment of blood vessel or other arterial lumen. Metal or metal alloy stents have been found useful in the treatment or repair of blood vessels after a stenosis has been compressed by percutaneous transluminal coronary angioplasty (PTCA), percutaneous transluminal angioplasty (PTA) or removal by other means. Metal stents are typically delivered in a compressed condition to the target site, then deployed at the target into an expanded condition or deployed state to support the vessel.

The following terminology is used. When reference is made to a "stent", this term will refer to a metal or metal alloy structure, generally speaking, while a scaffold will refer to a polymer structure. It is understood, however, that the art sometimes uses the term "stent" when referring to either a metal or polymer structure.

Metal stents have traditionally fallen into two general categories—balloon expanded and self-expanding. The later type expands to a deployed or expanded state within a vessel when a radial restraint is removed, while the former relies on an externally-applied force to configure it from a crimped or stowed state to the deployed or expanded state.

Self-expanding stents formed from, for example, shape memory metals or super-elastic alloys such as nickel-titanium (NiTi) which are designed to automatically expand from a compressed state when the radial restraint is withdrawn or removed at the distal end of a delivery catheter into the body lumen, i.e. when the radial restraint is withdrawn or removed. Typically, these stents are delivered within a radially restraining polymer sheath. The sheath maintains the low profile needed to navigate the stent towards the target site. Once at the target site, the sheath is then removed or withdrawn in a controlled manner to facilitate deployment or placement at the desired site. Examples of self-expanding stents constrained within a sheath when delivered to a target site within a body are found in U.S. Pat. No. 6,254,609, US 20030004561 and US 20020052640.

Balloon expanded stents, as the name implies, are expanded upon application of an external force through inflation of a balloon, upon which the stent is crimped. The expanding balloon applies a radial outward force on the luminal surfaces of the stent. During the expansion from a crimped or stowed, to deployed or expanded state the stent undergoes a plastic or irreversible deformation in the sense that the stent will essentially maintain its deformed, deployed state after balloon pressure is withdrawn.

Balloon expanded stents may also be stored within a sheath, either during a transluminal delivery to a target site or during the assembly or in the packaging of the stent-balloon catheter delivery system. The balloon expanded stent may be contained within a sheath when delivered to a target site to minimize dislodgment of the stent from the balloon while en route to the target vessel. Sheaths may also be used to protect a drug eluting stent during a crimping process, which presses or crimps the stent to the balloon catheter. When an iris-type crimping mechanism, for example, is used to crimp a stent to balloon, the blades of the crimper, often hardened metal, can form gouges in a drug-polymer coating or even strip off coating through interaction similar to forces at play when the blades and/or stent struts are misaligned during the diameter reduction. Examples of stents that utilize a sheath to protect the stent during a crimping process are found in U.S. Pat. No. 6,783,542 and U.S. Pat. No. 6,805,703.

A polymer scaffold, such as that described in US 20100004735 may be made from a biodegradable, bioabsorbable, bioresorbable, or bioerodable polymer. The terms biodegradable, bioabsorbable, bioresorbable, biosoluble or bioerodable refer to the property of a material or stent to degrade, absorb, resorb, or erode away after the scaffold has been implanted at the target vessel. The polymer scaffold described in US 2010/0004735, as opposed to a metal stent, is intended to remain in the body for only a limited period of time. In many treatment applications, the presence of a stent in a body may be necessary for a limited period of time until its intended function of, for example, maintaining vascular patency and/or drug delivery is accomplished. Moreover, it is believed that biodegradable scaffolds, as opposed to a metal stent, allow for improved healing of the anatomical lumen and reduced incidence of late stent thrombosis. For these reasons, there is a desire to treat a vessel using a polymer scaffold, in particular a bioerodible polymer scaffold, as opposed to a metal stent, so that the prosthesis's presence in the vessel is for a limited duration. However, there are numerous challenges to overcome when developing a delivery system having a polymer scaffold.

Polymer material considered for use as a polymeric scaffold, e.g. poly(L-lactide) ("PLLA"), poly(L-lactide-co-glycolide) ("PLGA"), poly(D-lactide-co-glycolide) or poly(L-lactide-co-D-lactide) ("PLLA-co-PDLA") with less than 10% D-lactide, and PLLD/PDLA stereo complex, may be described, through comparison with a metallic material used to form a stent, in some of the following ways. A suitable polymer has a low strength to weight ratio, which means more material is needed to provide an equivalent mechanical property to that of a metal. Therefore, struts must be made thicker and wider to have the required strength for a stent to support lumen walls at a desired radius. The scaffold made from such polymers also tends to be brittle or have limited fracture toughness. The anisotropic and rate-dependant inelastic properties (i.e., strength/stiffness of the material varies depending upon the rate at which the material is deformed) inherent in the material only compound this complexity in working with a polymer, particularly, bio-absorbable polymer such as PLLA or PLGA. Challenges faced when securing a polymer scaffold to a delivery balloon are discussed in U.S. patent application Ser. No. 12/861,719.

When using a polymer scaffold, several of the accepted processes for metal stent handling can no longer be used. A metal stent may be crimped to a balloon in such a manner as to minimize, if not eliminate recoil in the metal structure after removal from the crimp head. Metal materials used for stents are generally capable of being worked more during the crimping process than polymer materials. This desirable property of the metal allows for less concern over the metal stent—balloon engagement changing over time when the stent-catheter is packaged and awaiting use in a medical procedure. Due to the material's ability to be worked during the crimping process, e.g., successively crimped and released at high temperatures within the crimp mechanism, any propensity for elastic recoil in the material following crimping can be significantly reduced, if not eliminated, without affecting the stent's radial strength when later expanded by the balloon. As such, following a crimping process the stent-catheter assembly often does not need packaging or treatment to maintain the desired stent-balloon engagement and delivery profile. If the stent were to recoil to a larger diameter, meaning elastically expand to a larger diameter after the crimping forces are withdrawn, then significant dislodgment force could be lost and the stent-balloon profile not maintained at the desired diameter needed to deliver the stent to the target site.

While a polymer scaffold may be formed so that it is capable of being crimped in such a manner as to reduce inherent elastic recoil tendencies in the material when crimped, e.g., by maintaining crimping blades on the scaffold surface for an appreciable dwell period, the effectiveness of these methods are limited. Significantly, the material generally is incapable of being worked to the degree that a metal stent may be worked without introducing deployed strength problems, such as excessive cracking in the material. Recoil of the crimped structure, therefore, is a problem that needs to be addressed.

In view of the foregoing, there is a need to address the challenges associated with securing a polymer scaffold to a delivery balloon and maintaining the integrity of a scaffold-balloon catheter delivery system up until the time when the scaffold and balloon are delivered to a target site within a body.

SUMMARY OF THE INVENTION

The invention is directed to sheaths used to maintain polymer scaffold balloon engagement and delivery system profile as well as methods for assembly of a medical device including a balloon expandable polymer scaffold contained within a sheath. The invention is also directed to a sheath and methods for applying a sheath that enable the sheath to be easily removed by a medical professional, e.g., a doctor, in an intuitive manner without disrupting the crimped scaffold-balloon engagement or damaging the scaffold. Sheaths according to the invention are removed before the medical device is introduced into a patient.

Sheaths according to the invention are particularly useful for maintaining scaffold-balloon engagement and desired delivery profile following a crimping process for scaffolds formed at diameters larger than the delivered diameter are crimped down to achieve a smaller crossing-profile, or crimped diameter. A scaffold formed at a larger diameter, near to or greater than the intended deployed diameter, can exhibit enhanced radial strength when supporting a vessel, as compared to a scaffold formed nearer to a crimped diameter. A scaffold formed near to a deployed diameter, however, increases the propensity for elastic recoil in the scaffold following the crimping process, due to the shape memory in the material. The shape memory relied on for enhancing radial strength at deployment, therefore, also introduces greater elastic recoil tendencies for the crimped scaffold. Recoil both increases the crossing profile and reduces the scaffold-balloon engagement needed to hold the scaffold on the balloon. In one aspect, the invention is directed to maintaining the crossing profile and/or maintaining balloon-scaffold engagement for scaffolds formed near to a deployed diameter.

In another aspect, the invention is directed to a method of assembly of a catheter that includes crimping a polymer scaffold to a balloon of the catheter and within a short period of removal of the scaffold from the crimper placing a restraining sheath over the scaffold. The steps may further include applying an extended dwell time following a final crimping of the scaffold, followed by applying the restraining sheath. Both the crimping dwell time and applied restraining sheath are intended to reduce recoil in the crimped scaffold. The restraining sheath may include both a protecting sheath and a constraining sheath.

In another aspect, the invention is directed to a sterilized medical device, e.g., by E-beam radiation, contained within a sterile package, the package containing a scaffold crimped to a balloon catheter and a sheath disposed over the crimped scaffold to minimize recoil of the crimped scaffold. The sheath covers the crimped scaffold and extends beyond the distal end of the catheter. The sheath may extend at least the length of the scaffold beyond the distal end of the catheter. At the distal end of the sheath there is a portion configured for being manually grabbed and pulled distally of the catheter to remove the sheath from the catheter. In one embodiment, this portion is part of the protecting sheath. In another embodiment, the portion is part of the constraining sheath.

In another aspect, the invention is directed to an apparatus and methods for removing a sheath pair from a scaffold in a safe, intuitive manner by a health professional. According to this aspect of the invention, the sheath pair may be removed by a medical specialist such as a doctor without risk of the scaffold becoming dislodged from the balloon or damaged, such as when the sheath pair is accidentally removed in an improper manner by a health professional.

Sheaths arranged according to the invention provide an effective radial constraint for preventing recoil in a crimped scaffold, yet are comparatively easy to manually remove from the scaffold. A sheath that applies a radial constraint can be difficult to remove manually without damaging the crimped scaffold, dislodging or shifting it on the balloon. In these cases it is desirable to arrange the sheaths in a manner to apply an effective radial constraint yet make the sheaths capable of manual removal in a safe and intuitive manner. By making the sheath removal process easy to follow and intuitive, the possibility that a health professional will damage the medical device when removing the sheath is reduced.

According to another aspect of the invention a crimped scaffold is constrained within a protecting sheath and a constraining sheath. The protecting sheath, or protecting portion, protects the integrity of the crimped scaffold-balloon structure while the constraining sheath or constraining portion, is applied and/or removed from the crimped scaffold. Arranged in this manner a radial inward force may be applied to a crimped scaffold via a sheath, without risking dislodgement or shifting of the scaffold on the balloon when the sheath is manually removed.

According to another aspect, a sheath is formed to reduce frictional resistance when being removed from the scaffold. The sheath may include a constraining sheath disposed over a protecting sheath, or the sheath may be disposed directly over the scaffold. According to such embodiments, the reduced frictional resistance can minimize harmful shearing forces applied to the scaffold when the sheath is being removed.

According to another aspect of the invention, a sheath pair is used to impose a higher radial inward constraint on a crimped polymer scaffold than is possible using a single sheath that must be manually removed from the scaffold before the scaffold can be introduced into a patient.

According to another aspect of the invention, there is provided either a one or two piece sheath for constraining a scaffold. In either case, the sheath may include both a constraining portion and protecting portion.

According to another aspect of the invention, a sheath pair covering a crimped scaffold is removed by sliding a first sheath over a connected second sheath. After the first sheath has been displaced a sufficient distance, a connector connecting the sheaths withdraws the second sheath.

According to another aspect of the invention, a sheath includes a protecting portion that closes around a scaffold when a compression portion is inserted over the protecting portion. A handling portion, surrounding the compression portion, connected to the protecting portion, is included to remove the protecting portion from the scaffold, after the compression portion is removed.

According to another aspect of the invention, tabs are disposed between a constraining sheath and the scaffold. To remove the constraining sheath, the tabs are pulled radially outward to push the scaffold off of a distal end of the catheter. According to one such embodiment, the constraining sheath may be heat shrunk over the tabs and scaffold to provide a radially inward constraining force on the scaffold.

In accordance with the foregoing objectives, in one aspect of the invention there is a method for assembling a scaffold-balloon catheter, comprising providing a balloon-catheter having a scaffold crimped to the balloon; and constraining the crimped scaffold including placing the crimped scaffold within a protecting portion, and then placing the scaffold and protecting portion within a constraining portion, wherein the protecting portion and constraining portion are integral portions of a sheath; wherein the scaffold is configured for being passed through the body of a patient only after the sheath is removed from the crimped scaffold.

In another aspect, there is an apparatus, comprising a catheter assembly having a distal end and including a scaffold comprising a polymer crimped to a balloon; a sheath disposed over the scaffold, the sheath applying a radial inward force on the crimped scaffold to limit recoil of the scaffold, the sheath comprising a protecting portion having a distal end, a constraining portion disposed over the protecting portion, and a connector portion connecting the protecting portion and constraining portion; wherein the apparatus is configured for being passed through the body of a patient only after the sheath is removed.

In another aspect, there is method for assembling a scaffold-balloon catheter, comprising providing a balloon-catheter having a scaffold crimped to the balloon; and constraining the crimped scaffold using a two-piece sheath, including placing the crimped scaffold within a protecting portion of the sheath, then placing a constraining portion of the sheath over the protecting portion; wherein the scaffold is configured for being passed through the body of a patient only after the constraining portion and protecting portion are removed from the crimped scaffold.

In another aspect, there is an apparatus, comprising a catheter assembly having a distal end and including a scaffold comprising a polymer crimped to a balloon; a two-piece sheath disposed over the scaffold, the sheath applying a radial inward force on the crimped scaffold to limit recoil of the scaffold, the sheath comprising a protecting portion, and a constraining portion disposed over the protecting portion; wherein the apparatus is configured for being passed through the body of a patient only after the two-piece sheath is removed.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

BRIEF DESCRIPTION OF THE DRAWINGS

FIG. 5 is a side view of a polymer scaffold-balloon catheter assembly (medical device) with a pair of sheaths placed over the crimped scaffold according to an alternative embodiment.

FIG. 6A illustrates a side view of the sheath pair of FIG. 5.

FIGS. 7A-7C show front and side views of a constraining sheath having an inner surface for reducing friction between the constraining sheath and a protecting sheath according to alternative embodiments.

FIGS. 8A-8B show front and side views of a constraining sheath having an inner surface for reducing friction between the constraining sheath and a protecting sheath according to another alternative embodiment.

DETAILED DESCRIPTION OF EMBODIMENTS

A polymer scaffold according to a preferred embodiment is formed from a radially expanded or biaxially expanded extruded PLLA tube. The scaffold is laser cut from the expanded tube. The diameter of the tube is preferably selected to be about the same, or larger than the intended deployed diameter for the scaffold to provided desirable radial strength characteristics, as explained earlier. The scaffold is then crimped onto the balloon of the balloon catheter. Preferably, an iris-type crimper is used to crimp the scaffold to the balloon. The desired crimped profile for the scaffold is ½ or less than ½ of the starting (pre crimp) diameter of the expanded tube and scaffold. In the embodiments the ratio of the starting diameter (before crimping) to the final crimp diameter may be 2:1, 2.5:1, 3:1, or higher. For example, the ratio of starting diameter to final crimped diameter may be greater than the ratio of the deployed diameter to the final crimped diameter of the scaffold, e.g., from about 4:1 to 6:1.

The pre-crimp memory in the scaffold material following crimping will induce some recoil when the scaffold is removed from the crimper. While a dwell period within the crimper can reduce this recoil tendency, it is found that there is residual recoil that needs to be restrained while the scaffold is awaiting use. This is done by placing a restraining sheath over the scaffold immediately after the crimper blades are released and the scaffold removed from the crimper head. This need to reduce recoil is particularly evident when the diameter reduction during crimping is high, since for a larger starting diameter compared to the crimped diameter the crimped material can have higher recoil tendencies. Examples of polymers that may be used to construct sheaths described herein are Pebax, PTFE, Polyethelene, Polycarbonate, Polyimide and Nylon. Examples of restraining sheaths for polymer scaffold, and methods for attaching and removing restraining sheaths for polymer scaffold are described in U.S. application Ser. No. 12/916,349.

Figure 1:
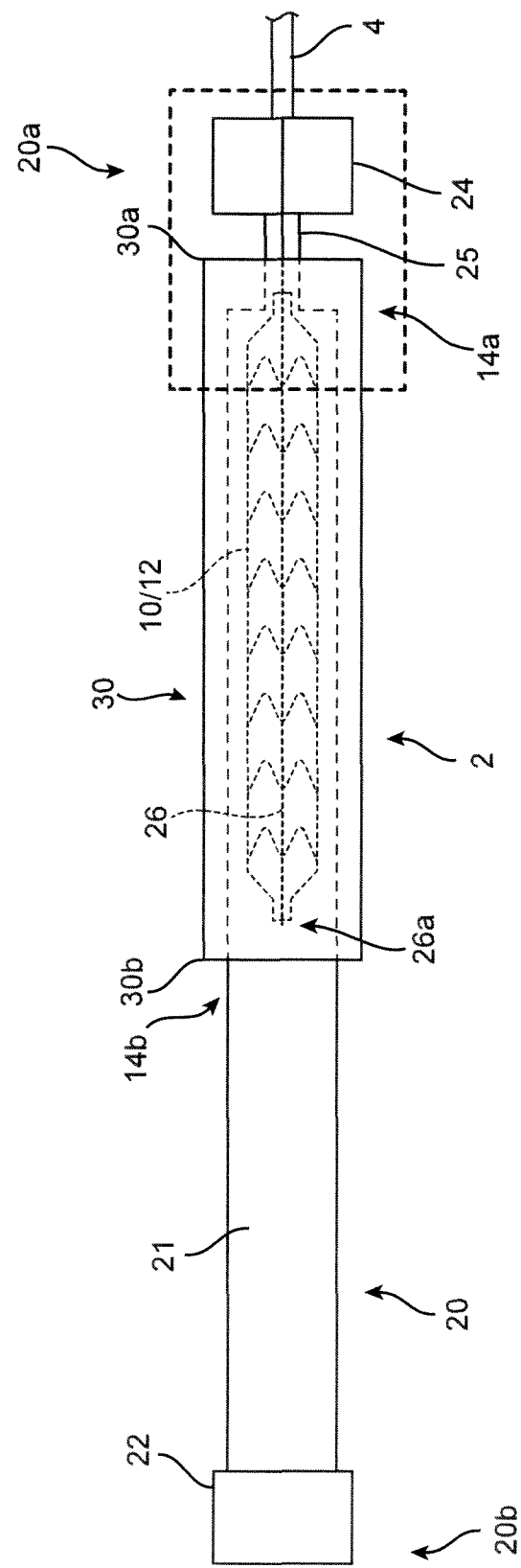
FIG. 1 is a side view of a polymer scaffold-balloon catheter assembly (medical device) with a pair of sheaths placed over the crimped scaffold.

FIG. 1 shows a side view of a distal portion of a scaffold-balloon catheter assembly 2. The catheter assembly 2 includes a catheter shaft 4 and a scaffold 10 crimped to a delivery balloon 12. As shown there are two separate sheaths 20, 30 disposed over the scaffold 10. The scaffold 10 is contained within a protecting sheath 20 and a constraining sheath 30, which is slid over the outer surface of the protecting sheath 20 to position it over the scaffold 10. Before inserting the catheter assembly 2 distal end within a patient, both the constraining sheath 30 and protecting sheath 20 are removed by a health professional.

The sheaths 20, 30 provide an effective radial constraint for reducing recoil in the crimped scaffold 10. Yet the sheaths 20, 30 are also easily removed by a health professional at the time of a medical procedure by pulling the outer sheath 30 towards the distal end of the scaffold 10 and balloon 12. This action will be described in more detail later. It is a similar motion to the removal technique required for other coronary device products, where a single, non-constraining sheath is used to cover and protect the stent. In those cases the sheath is grasped by the doctor or technician's gloved hands and pulled off towards the distal end of the device. A sheath that applies a radial constraint can be difficult to manually remove without adversely affecting the structural integrity of the medical device. In these cases, it is desirable to arrange the sheaths so that special handling is not required by the health professional when the sheath is manually removed. By making the sheath removal process easy to follow or intuitive, the possibility that a health professional will damage the medical device by improperly removing the sheath is reduced.

The constraint imposed by the sheaths 20, 30 maintain the scaffold 10 at essentially the same, or close to the same diameter it had when removed from the crimping mechanism, i.e., the crimped crossing profile, which is needed for traversing tortuous vessels to deliver the scaffold 10 to a target location in a body. The sheath 30 is tightly fit over the sheath 20 and scaffold 10 so that the radial inward force applied on the scaffold 10 can prevent or reduce recoil in the scaffold 10. The health professional may then remove both sheaths at the time of the medical procedure. As such, any potential recoil in the scaffold 10 prior to using the medical device is minimized.

The sheath 30, although imposing a tight fit on the scaffold 10 (through sheath 30), can be easily removed by a health professional without risk of the scaffold 10 being accidentally pulled off of the balloon 12. This is accomplished by the manner in which the sheath 20 is positioned and removed from the scaffold 10. If there are excessive pulling forces on the scaffold 10 when sheaths are removed, the scaffold 10 may dislodge from a balloon 12, or shift on the balloon 12, thereby reducing scaffold-balloon engagement relied on to hold the scaffold 10 to the balloon 12.

When the scaffold 10 is constrained by sheath 30, as in FIG. 1, the constraining sheath 30 is located over the section of the protecting sheath 20 where the crimped scaffold 10 is found. This sheath 30 is made from a polymer tube material having a thickness and pre-stressed inner diameter size suitably chosen to cause the sheath 30 to apply a radially inward directed force on the scaffold 10. The thicker the tube and the smaller the pre-stressed inner diameter size for the sheath 30 the higher this constraint will be on the scaffold 10. However, the sheath 30 thickness should not be too thick, nor its inner diameter too small as this will make it difficult to slide the sheath 30 over, or remove the sheath 30 from the scaffold 10. If excessive force is needed to reposition the sheath 30, the scaffold 10 can dislodge from the balloon 12 or become damaged when the sheath 30 is moved.

If only the single sheath 30 were used to constrain the scaffold 10, i.e., the sheath 20 is not present, the amount of preload that the sheath 30 could apply to the scaffold 10 without affecting scaffold-balloon engagement would be limited. However, by introducing the protecting sheath 20 between the scaffold-balloon surface and sheath 30 the sheath 30 can impose a higher preload on the scaffold 10 without risk to the integrity of the scaffold-balloon engagement when the sheath 30 is applied to and/or removed from the scaffold 10. The protecting sheath 20 therefore serves to protect the integrity of the scaffold-balloon structure as the sheath 30 is repositioned relative to the scaffold 10.

Figure 3A:
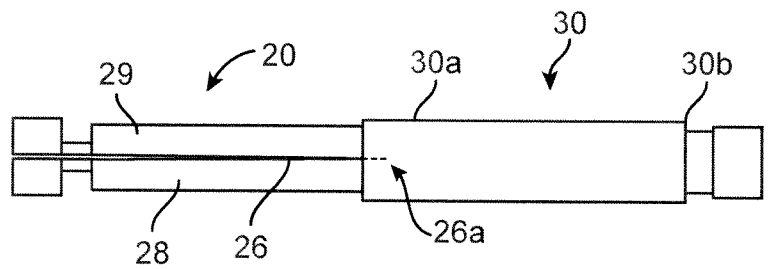
FIGS. 3A-3D illustrate a method of securing the sheath pair of FIG. 2A to a distal end of the catheter assembly of FIG. 1.
Figure 3B:
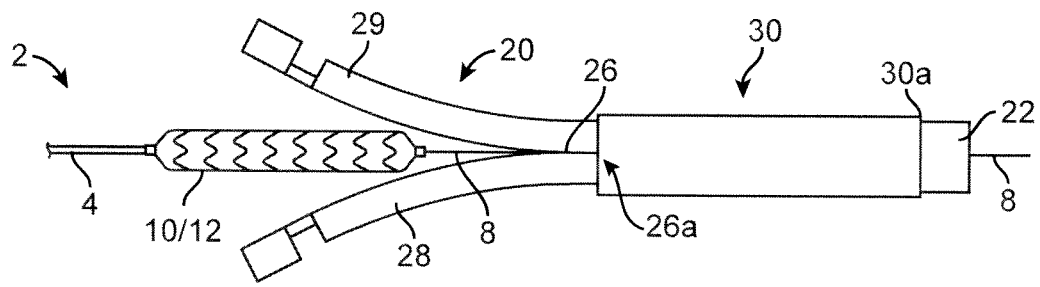
Figure 4A:
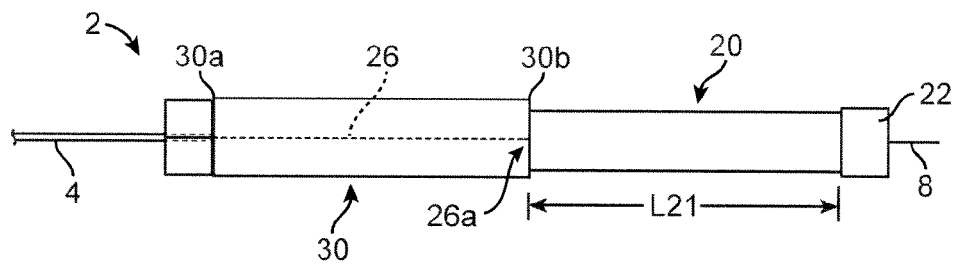
FIGS. 4A-4C illustrate a method of removing the sheath pair of FIG. 2A from the distal end of the catheter assembly of FIG. 1.
Figure 4B:
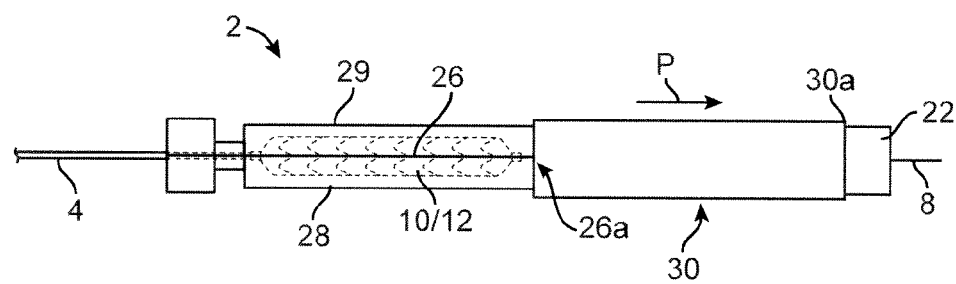
Figure 4C:
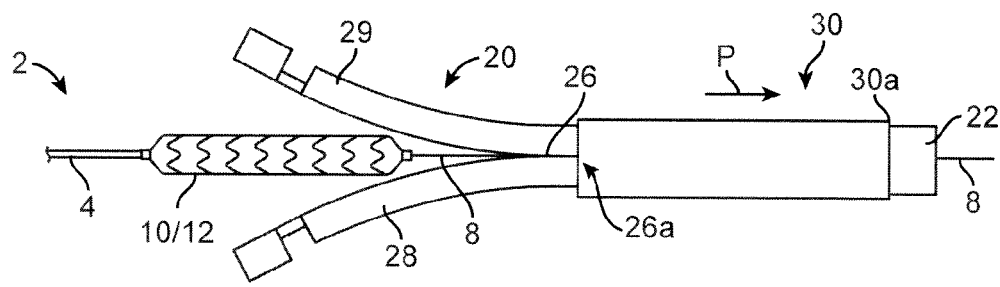

The protecting sheath 20 extends over the entire length of the scaffold (as shown) and beyond the distal tip of the catheter assembly 2 (i.e., the distal tip of the catheter assembly with sheaths 20, 30 removed, as can be more easily seen in FIGS. 3B and 4C), for reasons that will become apparent. The protecting sheath 20 is preferably formed from a unitary piece of polymer material, which is shaped to form differently sized portions 22, 24 and 25 for protecting the scaffold/balloon 10/12.

At the distal end 20b of sheath 20 there is a raised end 22 in the form of a cylinder section having a larger diameter than the body portion 21 of the sheath 20 to the right of end 22 which covers the scaffold 10 in FIG. 1. As such, raised end 22 provides an abutting surface with respect to distal movement of sheath 30, i.e., end 30b of sheath 30 abuts end 22 when sheath 30 is moved to the left in FIG. 1. End 22 may alternatively take the shape of a cone with the largest diameter end of the cone being the most distal end of the sheath 20. The raised end 22 is used to remove the sheaths 20, 30, as explained below.

The protecting sheath 20 has a cut 26, extending from the proximal end 20a to a location about at the distal the tip of the catheter assembly 2. The cut 26 forms an upper and lower separable halve 28, 29 of the sheath 20. These halves 29, 28 are configured to freely move apart when the sheath 30 is positioned towards the distal end 20b. The location 26a may be thought of as a living hinge 26a about which the upper half 29 and lower half 28 of the sheath 20 can rotate, or deflect away from the scaffold 10. When sheath 30 is moved distally of the scaffold 10 in FIG. 1, the halves 28, 29 will tend to open up naturally, due to the preload applied by sheath 30 near hinge 26a (the separable halves 28, 29 can be more clearly seen in FIGS. 2A-2D). This arrangement for halves 29, 28 allows sheath 20 it to be easily removed from the scaffold 10 with minimal disruption to scaffold-balloon structural integrity, after sheath 30 is moved to distal end 20b. When sheath 30 is being fitted over the scaffold 10 or removed from the scaffold 10, the presence of the halves 28, 29 prevent direct contact between the sliding sheath 30 and the surface of the scaffold 10.

At a proximal end 20a of sheath 20 there are portions 24 and 25 formed when the combined proximal ends of halves 28, 29 are brought together as in FIG. 1. When the halves 28, 29 are brought together the portions 24 and 25 take the form of a stepped or notched portion 25 and a raised end 24 similar to end 22, as shown in FIG. 1 and the cross-sectional view of the proximal end 20a of the assembly of FIG. 1A. The notched or stepped portion 25 has an outer diameter less than the outer diameter of the portion 21 of the sheath that covers the scaffold 10, as well as the outer diameter of the scaffold/balloon 10/12. The raised end 24 has a diameter that is greater than the body portion 21. The raised end 24 provides an abutment or stop 24a preventing the proximal end 30a of the sheath 30 from moving to the right in FIG. 1. As such, the end 24 prevents the sheath 30 from sliding off of the scaffold 10. The portion 24 also serves to identify the approximate location of the sheath 30 proximal end 30a so that it is fitted over the scaffold 10 and balloon 12. Sheath 30 has a length about equal to the length of the portion 25 plus the scaffold/balloon length so that when end 30a abuts end 24 the sheath 30 will properly cover the entire scaffold/balloon 10/12 length.

Figure 1A:
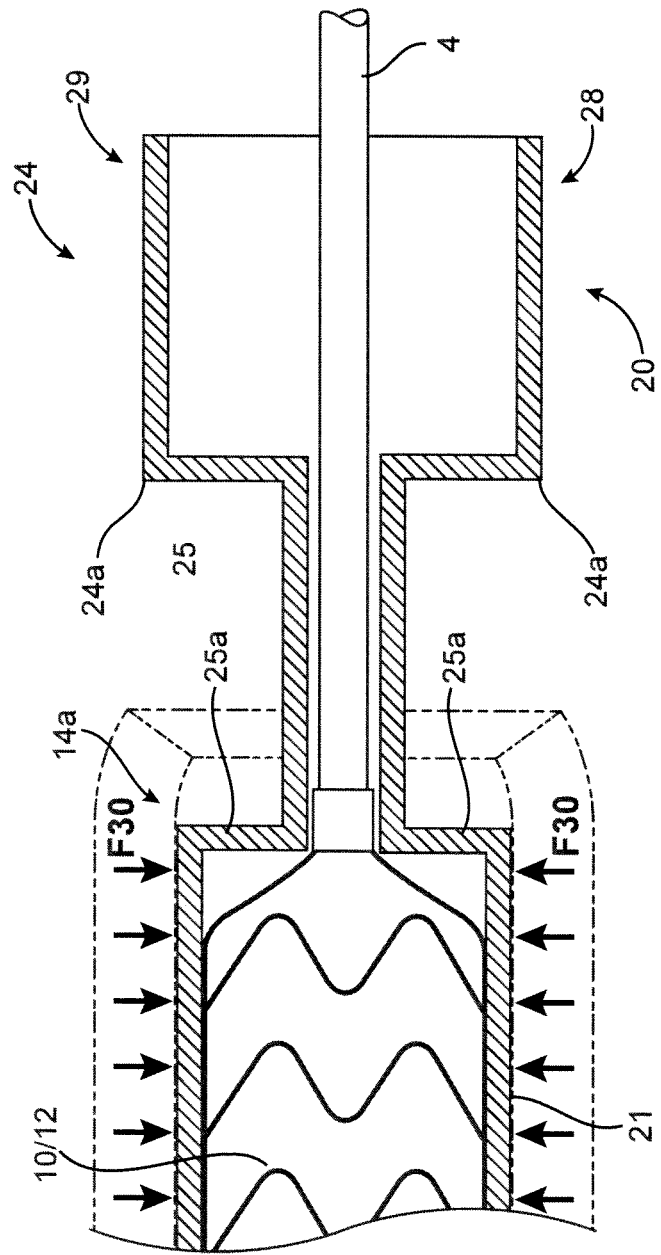
FIG. 1A shows a side view cross-section of a portion of the device of FIG. 1 at a proximal end thereof.

Portion 25 discourages removal of the sheath 20 prior to removal of sheath 30 from the scaffold 10. FIG. 1A shows a close-up of the proximal end 20a from FIG. 1 with the sheath 30 (shown in phantom) replaced by the inwardly directed preload F30 it applies to sheath portion 21 when positioned over the scaffold 10. A distal end of portion 25 forms a ledge 25a. When sheath 30 is positioned over the scaffold 10 the inwardly directed preload F30 applied to sheath portion 21 urges the halves 29, 28 together. With the halves 28, 29 urged together, the scaffold/balloon proximal end 14a blocks movement of the sheath 20 to the left in FIG. 1A by interfering with the movement of the ledge 25a to the left. Thus, if a user attempts to pull the sheath 20 off prior to removing the sheath 30 from the scaffold 10 area (which can damage the scaffold/balloon integrity), there will be resistance to this movement due to the ledges 25a abutting the balloon proximal end 14a (the ledge 25a thus may be thought of as an interference or interfering ledge part of the sheath 20). This resistance should indicate to the user that the sheaths 20, 30 are being removed in an improper manner. When the sheaths 20, 30 are removed properly, the first sheath 30 is moved to the distal end 20b of the sheath 20 (thereby removing the preload F30) so that the halves 28, 29 freely open up to allow the ledge 25a to easily pass over the scaffold 10 so that sheath 20 is removed without resistance. The user is thereby informed that the sheath 20 is removed properly when there is no resistance to removing the sheath 20 from the balloon-catheter assembly 2.

Thus, scaffold-balloon integrity is protected by the presence of the halves 28, 29 and the notched portion 25, as discussed above. The extended length of sheath 20, beyond the tip of the catheter assembly 2, e.g., is about equal to a length of the scaffold 10, the length of the sheath 30 or greater than both. This length beyond the distal tip facilitates an intuitive sliding removal or attachment of the sheath 30 from/to the scaffold 10 by respectively sliding the sheath 30 along the sheath 20 extension that is beyond the distal tip of the catheter assembly 2. The length of the sheath 20 that extends beyond the distal end 4 of the catheter assembly 2 (length L21 in FIG. 4A) may depend on the choice of sheaths used. For example, from the perspective of the health professional removal process, if the sheath 20 is more stiff (e.g., higher wall thickness and/or modulus) relative to the sheath 30 then the length beyond distal end 4 for sheath 20 may be longer so that the halves 28, 29 of sheath 20 can be more safely displaced from the scaffold 10 by clearing the sheath 30 more distally of the scaffold 10. If the sheath 30 wall thickness and/or modulus is higher relative to sheath 20 than the length may be shorter since the sheath 30 will tend to naturally open up the halves 28, 29 as it is moved distally of the distal tip of the catheter assembly 2. Also, a thicker or higher modulus sheath 20 and/or sheath 30 may be desirable to increase the resistance to improper removal of sheath 20, e.g., as when a user attempts to remove sheath 20 with, or before removing sheath 30 from the scaffold 10 (as discussed earlier).

Figure 2A:
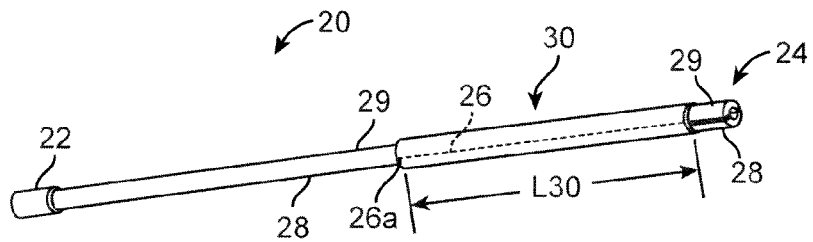
FIG. 2A is a perspective view of the sheath pair of FIG. 1.
Figure 2B:
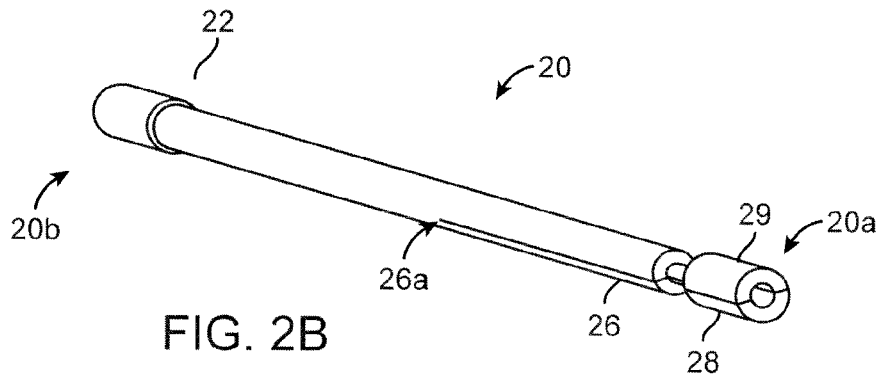
FIGS. 2B-2D show a side view, and first and perspective views of a protecting sheath of the sheath pair of FIG. 2A.
Figure 2C:
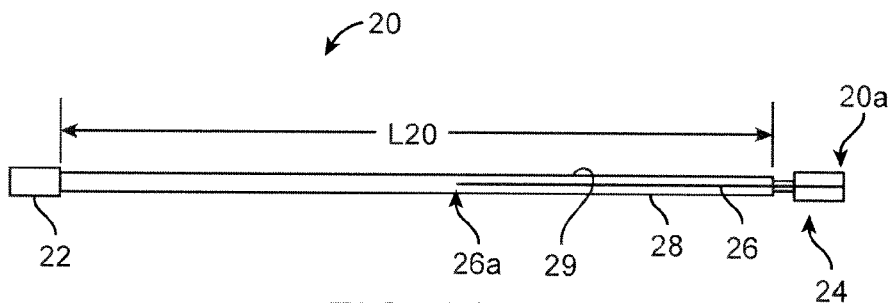
Figure 2D:
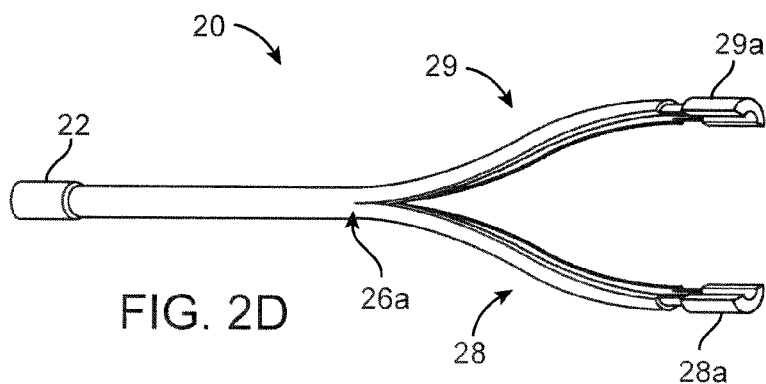

Referring to FIGS. 2B-2D, there are shown various views of the sheath 20. FIG. 2A shows the sheath 20 with the sheath 30. As mentioned above sheath 30 is sized to have a length L30 such that sheath 30 applies a sufficiently uniform radial inward force or preload on the scaffold 10 when end 30a abuts end 24a. The length L30 should therefore be slightly greater than the length of the scaffold-balloon structure. The sheath 30 can be slid towards or away from the scaffold location (i.e., its location in FIG. 2A or FIG. 1) over the sheath outer surface 20. As noted earlier, the sheath 20 has separable upper and lower halves 29, 28 formed by a cut 26 made across the tube forming sheath 20. FIG. 2D is a perspective view of the upper and lower halves 28, 29 separated from each other. As can be appreciated from this view, the halves 28, 29 rotate about the hinge 26a when they separate. FIGS. 2B and 2C show an additional side and perspective view, respectively, of the sheath 20 showing the aforementioned structure, including the portions of notched or stepped portion 25 and end 24 discussed earlier.

The length L20 in FIG. 2C should be chosen to extend over the scaffold 10 length as well as a sufficient distance beyond the scaffold 10 so that the sheath 30 can be pushed onto the scaffold 10, and removed from the scaffold 10 while the halves 28, 29 are disposed over the scaffold 10. The length L20 may be at least twice the length of sheath 30, i.e., L20=2*L30, to achieve this purpose. This length should be sufficient to allow the upper and lower halves 28, 29 to peel or rotate about the living hinge 26a and freely away from the scaffold surface (as in FIG. 2D) without interfering with the sheath 30.

As mentioned earlier, a thicker tube and smaller inner diameter for sheath 30 will cause the sheath 30 to apply a greater pre-load on the scaffold 10. The sheath 30 thickness and/or inner diameter size is selected with the sheath 20 in mind. That is, the sizing of one can determine what sizing to use for the other, based on achieving an appropriate balance among the amount of pre-load F30 (FIG. 1A) desired, the ease in which the sheath 30 can be placed over or removed from the scaffold 10 location, increasing resistance to improper removal of sheath 20 (ledge 25a abutting proximal end 14a, as discussed above) and avoiding disruption to the integrity of the scaffold-balloon structure, e.g., pulling the scaffold 10 off the balloon when the sheath 30 is being removed. For example, if a relatively thin and/or low modulus tube is used for sheath 20 (as compared to sheath 30), the sheath 30 will impose a higher localized pre-load on the scaffold 10. And the scaffold 10 is more likely to be affected by sheath 30 movement because the sheath 20 easily deforms under the movement of the sheath 30. If the sheath 20 is made thick and/or a higher modulus tube material is used for sheath 20 (compared to sheath 30) the scaffold 10 will not be as affected by movement of the sheath 30. And local changes in pre-load on the scaffold 10 will tend to be lower since the sheath 20 does not deform as easily under the movement of the sheath 30.

Referring to FIGS. 3A-3D, methods of assembly using the sheaths 20, 30 (sheath pair) are now described. The scaffold 10 is crimped to the balloon 12 of the catheter assembly 2 using a crimping mechanism. As noted above, for a polymer scaffold the diameter reduction during crimping may be 2:1, 2.5:1, 3:1, 4:1 or higher. This diameter reduction introduces high stresses in the scaffold structure. The memory in the material following crimping causes recoil of the scaffold structure, as discussed earlier.

One can incorporate lengthy dwell times within the crimper, e.g., after the final crimp step, to allow stress-relaxation to occur in the structure while heated crimper blades are maintaining a fixed diameter and temperature to facilitate stress relaxation. Both the dwell period and the imposition of a constraining sheath over the crimped scaffold after crimping helps to reduce recoil after crimping. Crimping of the scaffold 10 to the balloon 12 including desirable dwell times and temperatures that can affect stress relaxation and recoil after crimping are disclosed in U.S. patent application Ser. No. 12/861,719, U.S. patent application Ser. No. 13/089,225 and U.S. patent application Ser. No. 13/107,666.

The sheath pair, shown in FIG. 3A, is placed on a mandrel 8 before being attached to the catheter assembly 2. The mandrel 8 is passed through the catheter shaft 4 guidewire lumen (not shown), and exits at the distal end of the catheter assembly 2. The sheath pair is then placed on the mandrel 8 distally of the catheter assembly 2. The mandrel 8 is then used to guide the sheath pair over the scaffold-balloon 10/12 as illustrated in FIGS. 3B-3D.

Referring to FIG. 3B, the distal end 30a of the sheath 30 is adjacent to the raised end 22 of the sheath 20. In this configuration the halves 28, 29 can freely open or close. The sheath pair is then brought towards the scaffold-balloon 10/12. The halves 28, 29 easily deflect over the scaffold-balloon 10/12. The sheath pair may be slid towards the scaffold-balloon 10/12 as follows. Holding the catheter assembly 2 stationary, grasping the mandrel 8 with one hand and the sheath pair with the other hand and sliding the sheath pair over the mandrel 8 until the halves 28, 29 are located over the scaffold-balloon 10/12 as shown in FIG. 3C. When properly positioned, the portions 24, 25 are positioned with respect to proximal end 14a as shown in FIG. 1A.

Figure 3C:
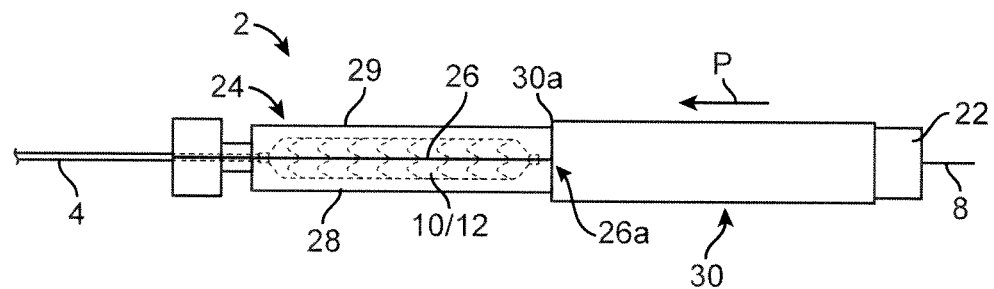
Figure 3D:
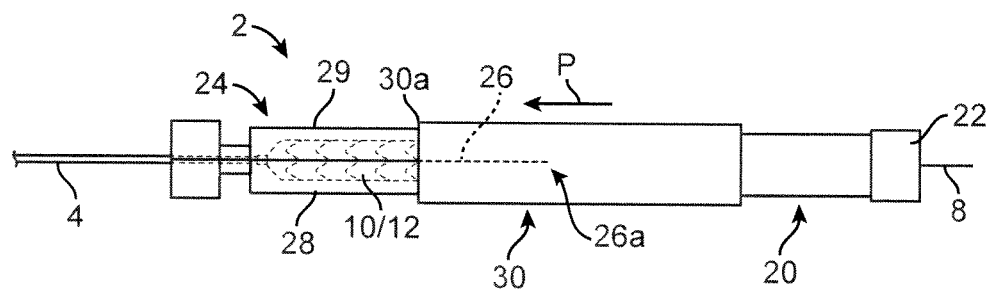

Referring to FIGS. 3C-3D, once the halves 28, 29 are located properly over the scaffold-balloon 10/12 to protect this structure, the constraining sheath 30 can be pushed over the scaffold-balloon 10/12 (as indicated in FIGS. 3C-3D by P). The sheath 30 may be pushed over the scaffold-balloon 10/12 in the following manner. The raised end 22 and mandrel 8 are grasped with one hand to hold the two stationary. Then, using the other hand the sheath 30 is pushed over the scaffold-balloon 10/12 until the end 30a of sheath 30 is disposed adjacent to, or abuts the raised end 24 of the sheath 20, which indicates the proximate location of the proximal end 14a of the balloon-scaffold 10/12. Alternatively, the portion 24 and catheter shaft 4 may be simultaneously held with on hand, while the sheath 30 is pushed towards the scaffold 10 with the other hand. By grasping the portion 24 with the catheter shaft 4, the halves 28, 29 are held in place relative to the scaffold 10 while the sheath 30 is being pushed over the scaffold 10.

The catheter assembly 2 with sheaths arranged as in FIG. 4A is packaged and sterilized. At the time when the catheter assembly is to be used in a medical procedure the package is opened and the sheath pair removed from the distal end. The catheter assembly 2 is not configured for being introduced into the patient until the sheath pair is removed. FIGS. 1, 1A and 4A depict the arrangement of the sheaths 20, at the distal end of the catheter assembly 2 when the packaged and sterile medical device is received by a health professional. Examples of such sterile packaging is found in U.S. patent publication no. US 2008-0010947. The sheath 20 extends well-beyond the distal tip of the catheter assembly 2 such that it overhangs this distal tip. The overhanging portion of the sheath 20, which has a length of more than L21 (FIG. 4A), is provided to facilitate a safe and intuitive removal of the sheath pair by a health professional, thereby reducing the chances that the sheath pair are removed improperly.

Referring to FIGS. 4B-4C, methods for removing the sheath pair from the scaffold-balloon 10/12 by the health professional are now described. These illustrations refer to moving the sheath pair over the mandrel 8; however, a mandrel 8 is not necessary. The sheath pair may be safely removed from the catheter assembly 2 without using a mandrel 8.

A sterilized and packaged catheter assembly with sheaths 20, 30 positioned as shown in 4A typically includes the stiffening mandrel 8 in the catheter shaft 4 lumen to provide bending stiffness for shaft 4. A distal end of the mandrel 8 has a curled end, or an extension/stop at the distal end (not shown), which is used to manually withdraw the mandrel 8 from the catheter shaft 4 lumen by pulling the mandrel 8 towards the distal tip of the catheter assembly 2. In the following example the sheaths 20, 30 are removed. The proscribed steps preferably also include the act of removing the mandrel 8 from the catheter shaft lumen by, e.g., simultaneously gripping the raised end 22, sheath 30 and mandrel 8.

First, the sheath 30 is pulled away from the scaffold-balloon 10/12 structure, where it is shown positioned in FIG. 4A. The sheath 30 may be withdrawn or pulled away from the scaffold-balloon 10/12 in the following manner. One hand grasps the raised end 22 and mandrel 8, to hold the two stationary, while the other hand grasps and pulls the sheath 30 towards the raised end 22. When the sheath 30 reaches the raised end 22 the halves 28, 29 should freely deflect away from the scaffold 10 surface, since a majority if not all of the cut 26 is to the left of the sheath 30 (FIG. 4B). At this point both sheaths 20, 30 can be simultaneously pulled away from the scaffold-balloon 10/12.

As an alternative, the sheaths 20, 30 may be removed by grasping the catheter assembly distal portion, e.g., the catheter shaft 4, and optionally portion 24 as well with one hand and grasping and pulling the sheath 30 distally of the catheter assembly 2 with the other hand. Once the sheath 30 has abutted the raised end 22 (and removing hand from portion 24, if being gripped with shaft 4), continued pulling on the sheath 30 distally can safely remove both sheaths without risk of dislodging the scaffold 10 from the balloon. The pulling of the sheath 30 distally, while it abuts the raised end 22, causes both the sheath 20 and the sheath 30 to be removed from the scaffold-balloon 10/12. The raised end 22 therefore functions as an abutment for removing both sheaths in a safe manner with minimal disruption to the crimped scaffold. This final pulling away of the sheath 20 from scaffold 10 may also simultaneously remove the stiffening mandrel 8 from the catheter shaft 4 lumen.

As discussed earlier, the assembly of sheaths 20, 30 discourages a health professional from removing the sheath 20 before sheath 30 is moved to end 22. For example, if a health professional were to pull on the end 22 while the sheath 30 is positioned over the scaffold, the ledges 25a abutting proximal end 14a will interfere with distal movement of the sheath (FIG. 1A). When this resistance is felt, this should indicate to the health professional that the sheath 20 is being removed in an improper manner. If the sheath 30 is first moved to end 22, then the sheath 20 can be pulled off of the catheter distal tip very easily since the halves 29, 28 (free of the preload F30) will easily open up and pass over the scaffold 10.

In an alternative embodiment of sheath 20, the raised end or stop 22 and 24 may be formed by a heat shrink process. In the examples above the stops 22, 24 were preferably formed when the tubing was formed, e.g., insert-molding the tube shape to produce the structure 22, 24 described in FIGS. 1-2. Alternatively, a constant-diameter tube may be formed. Radially stretched polymer rings are then placed at the proximal and distal ends 20a, 20b of sheath 20. Heat is then applied to the stretched rings, which causes the rings to return to about their pre-stretched diameter. This can secure the rings to the tube. With the extra material heat shrunk over the sheath 20 at ends 20a, 20b, there can be formed stops essentially the same in function and size as stops 24, 22, respectively (these heat shrunk stops will hereinafter be referred to as stops 24', 22'). Accordingly, the heat shrunk stop 24' can prevent proximal movement of the sheath 30 (as in the case of stop 24) and the heat shrunk stop 22' can provide an abutment for removal of the protecting sheath 20 with the constraining sheath 30 (as in the case of stop 22).

The sheath 20 may be constructed with heat shrunk stops 22', 24' as follows. First, a tube of length L20 is formed. The tube has a constant diameter except where the stepped down portion 25 is located. A pair of rings having a length about the same as the length of stops 22, 24 and a diameter smaller than the portion 21 of sheath 20 are then plastically deformed and placed over the desired location. Heat is then applied to the deformed rings and tube location where the rings will be attached, to cause the ring diameters to shrink back to about their original diameters, which was less than the diameter of portion 21, and bond to the tube, thereby securing the stops 24', 22' to the sheath 20 material. Once secured, the cut 26 may be made and the halves 28, 29 become separated. The half-portions of the heat shrunk stop 24' being located on each of the halves 28, 29.

An alternative to the sheath pair 20, 30 is depicted in FIGS. 5 and 6A-6C. According to this aspect of the disclosure, an outer constraining sheath (sheath 50) and inner protecting sheath 40 (sheath 40) are physically connected to each other to form a one piece sheath pair 40, 50. This one piece sheath pair offers several of the constraining sheath and protecting sheath advantages discussed in connection with the sheaths 20, 30. As such, the same discussion with regards to advantages of sheath pair 20, 30 applies to sheath pair 40, 50 unless stated otherwise.

Figure 6B:
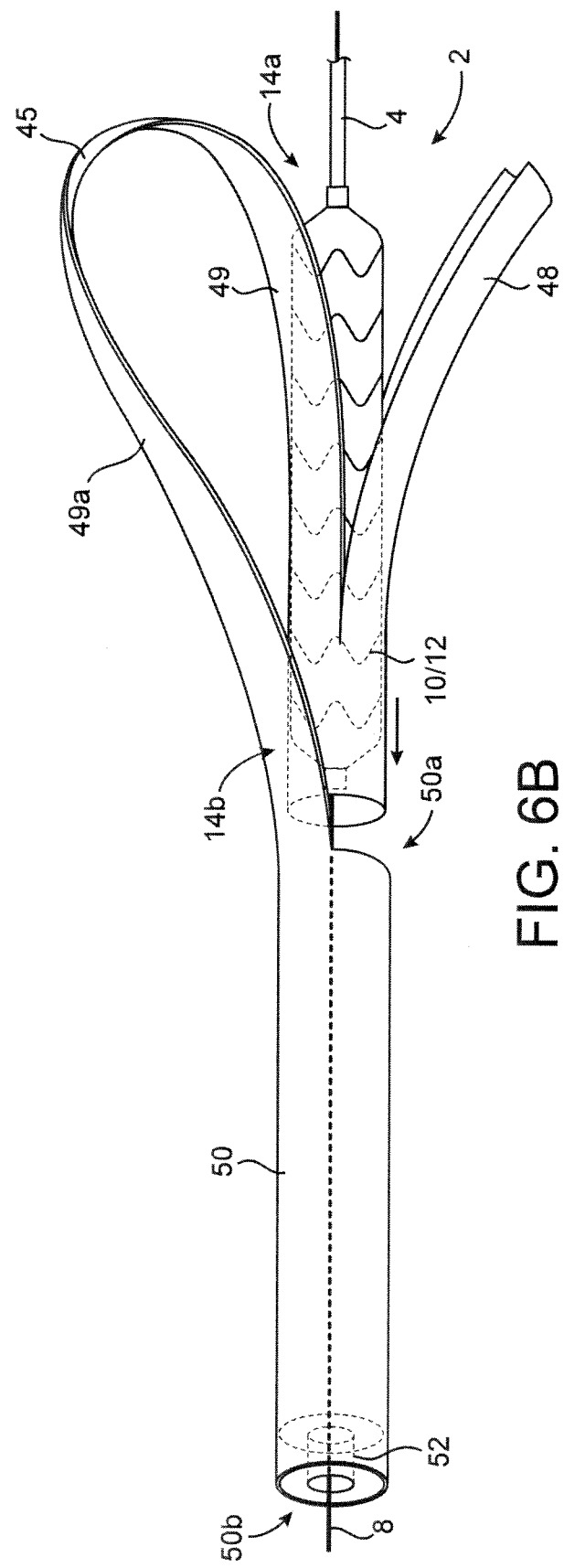
FIG. 6B illustrates a method of placing the sheath pair of FIG. 6A over the scaffold-balloon catheter assembly to arrive at the assembled view of FIG. 5.

The connection between the sheath pair 40, 50 is depicted in FIG. 6A by a hinge 45 and portion 49a, which hinge 45 can be a living hinge. The hinge 45 may be thought of, alternatively, as a portion of an upper half 49 of the sheath 40 (similar to upper half 29 of sheath 20) connected at its proximal end to the proximal end 50a of the sheath 50. By this connection to sheath 50 half 49 (or connector 49) functions as a protecting portion of sheath 40 for the scaffold when sheath 50 is placed over the scaffold 10, a connector connecting sheaths 40 and 50, and as a hinge for allowing sheath 40 to be inserted into sheath 50, as depicted in FIG. 6B. Thus, a one piece sheath pair 40, 50 can function in a similar manner as the separate sheath pair 20, 30 discussed earlier.

The outer sheath 50 length L50 (spanning from proximal end 50a to distal end 50b) is about the same as length L30 of sheath 30 or longer than sheath 30 for the reasons set out below. A length L40 for sheath 40 may be the same as L20, or longer. There are additional related features between sheath pair 20, 30 and sheath pair 40, 50. The constraining sheath, i.e., sheath 50, length L50 is at least the length of the scaffold/balloon 10/12. And sheath 40 has a hinge 46a for deflection of upper and lower halves 48, 49 away from the scaffold 10 after the sheath 50 has been withdrawn from the scaffold 10. Thus, as with sheath 20, sheath 40 includes a cut 46 to form halves 48, 49 and hinge point 46a.

Referring to FIG. 5, the scaffold/balloon 10/12 is within both the sheaths 40, 50 when the sheath 50 preload is applied to the scaffold/balloon 10/12, which helps to maintain the crimped profile and reduce recoil, as explained earlier. Unlike the assembly of FIG. 1, however, there is no extension of sheath 40 beyond the distal end 14b of the catheter assembly 2. Rather, the end 40b of sheath 40 is disposed at about the same location, or proximal of the sheath 50 distal end 50b when in an assembled state, e.g., as a packaged medical device. FIG. 6B depicts an extension of sheath 50 such that distal end 50b is distal of both of the distal ends 14b and 40a. In a similar fashion as stop 22 of sheath 20, the extension of sheath 50 can be gripped to withdraw sheath 40 from sheath 50, as explained below, without also gripping sheath 40.

The sheaths 40 and 50 may be formed from a single piece of tubing, or different tubing that is bonded or otherwise physically connected to each-other to form a one-piece sheath. When physically connected, or made from a single piece of tubing, a one-piece sheath has a protecting and constraining sheath portion that are integral in the sense that there is a mechanical engagement between the two. When made from a single piece of tubing the one-piece sheath may be thought of as formed from a unitary piece of material.

Figure 6C:
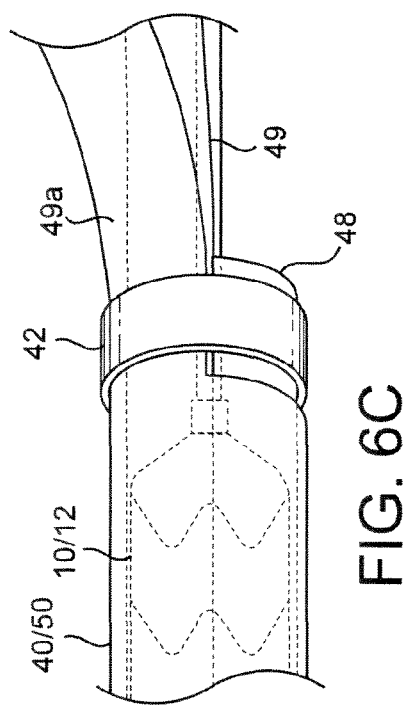
FIG. 6C shows a portion of the proximal end of the assembled device of FIG. 5 with a clamp used to secure the sheath pair of FIG. 5 in position relative to the scaffold-balloon catheter assembly according to an alternative embodiment.
Figure 6D:
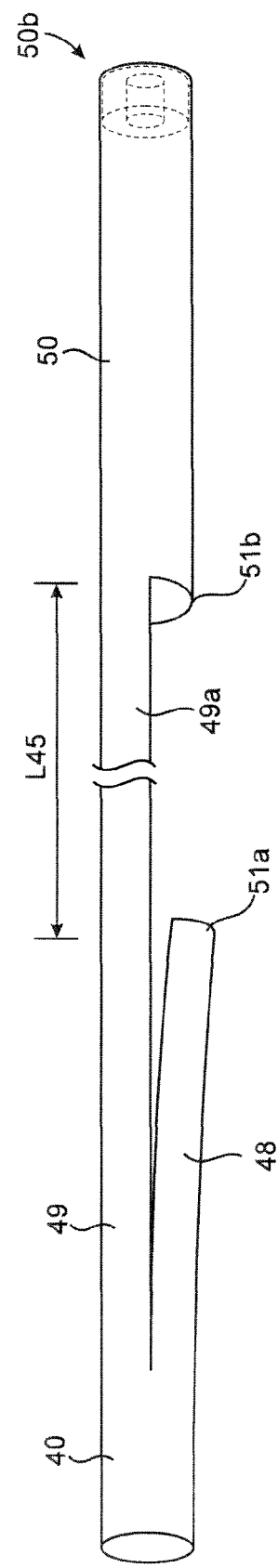
FIG. 6D shows the sheath pair of FIG. 6A when formed from a single piece of tubing.

Referring to the case of a one-piece sheath made from a single piece of tubing, the sheath construction may start with tubing cut or formed to size, as shown in FIG. 6D. The tubing has a length equal to the sum of the lengths, i.e., L40+L50+L45. The one end of the tube corresponds to the distal end of the sheath 50 and the other end of the tube corresponds to the distal end of the sheath 40. The cut 46 is made over the length extending from the hinge 46a to the proximal end 51b of the sheath 50 portion. The lower halve 48 of the sheath 40 is then separated from the proximal end 50a of the sheath 50 and the portion between 51a and 51b removed. The portion of length L45 may be retained, in which case lower half 48 extends to proximal end 51b. As mentioned earlier, the upper half 49 serves to connect the sheaths 40, 50, protect the scaffold 10 and provide a hinge 45 for articulating the sheath 40 relative to sheath 50 as shown in FIGS. 6A-6B. The sheath pair 40, 50 may then be placed over the scaffold-balloon 10/12 to provide the assembly illustrated in FIG. 5, which shares many of the same advantages as the assembly of FIG. 1.

The flexibility of hinge 45 and material forming the half 49 permits the arrangement shown in FIG. 5 where it can be appreciated that half 49 is folded over itself when both of the sheath pair 40, 50 are over the scaffold 10. Tubing that provides desired stiffness properties for applying a preload to the scaffold 10, protecting the scaffold 10 and with sufficient flexibility to enable the half 49 to fold over itself, or function as a hinge 45, as illustrated, is known in the art. In an alternative embodiment a desired tube thickness and/or stiffness may not easily function as a hinge 45. In this case, the half 49 may be weakened at the desired location or region of the hinge 45.

The prior discussion regarding tube thickness, diameter and/or modulus of material with regards to removal, preload, etc. in connection with sheaths 20, 30 applies equally to the sheath pair 40, 50. For instance, sheath 40 may have a different modulus, diameter and/or thickness from sheath 50 where the sheaths are formed from different tubing. When sheaths 40, 50 are made from different material, and/or have a different wall thickness or diameter the two may be joined or connected by a thermal bonding of the end 49*a* to sheath 50 proximal end 50*a*.

With reference to FIGS. 5, 6B and 6C methods of configuring the packaged or post-crimping catheter assembly (i.e., sheaths 40, 50 placed over the distal portion of the balloon-catheter after crimping or when being sterilized and awaiting use by a health professional, as depicted in FIG. 5) are discussed. The scaffold/balloon 10/12 or distal end 14*b* of the catheter assembly 2 is inserted into the sheath 40. The halves 48, 49 are free to open so that the scaffold-balloon 10/12 is easily received at the distal end 40*b* of the sheath 40. With the distal end 14*b* at about, or proximal to the distal end 40*b* the sheath 40 and catheter assembly 2 are then inserted into the sheath 50. When the sheath 40 and scaffold/balloon 10/12 are received within the sheath 50, the sheath 50 applies the desired preload on the scaffold/balloon 10/12 and the halves 48, 49 have come together over the scaffold/balloon 10/12. This assembly may be performed while a stiffening mandrel 8 extends through the guidewire lumen of the catheter shaft 4 (as was the case for sheaths 20, 30).

In alternative embodiments the sheath 50 may be constructed to have a stepped down diameter section 52 at the distal end 50*b*, which section 52 forms a stop (similar in form and function to the stops formed by section 25) that can prevent the sheath 40 from extending distally beyond the point where the stepped-down diameter begins. At the proximal end, a clamp 42 as depicted in FIG. 6C may be used to grip both the sheath 40 and sheath 50. The pressure on the shaft 4 (which preferably has a stiffening mandrel 8 extending there through) by the clamp 42 may be such as to prevent both distal and proximal movement of the sheath 50 relative to the sheath 40. In one example both the clamp 42 and stepped down distal end 52 of sheath 50 are used to facilitate an intuitive removal process by a health professional and ensure the sheath pair 40, 50 do not shift relative to each other while the packaged medical device awaits use.

Referring to FIGS. 5 and 6A-6C, a method of removal of the sheath pair 40, 50 begins with removing the clamp 42 from the proximal end. The clamp 42 applies a pressure force gripping the proximal ends of both sheaths 30, 50 to the catheter shaft 4. When removed the sheaths 40, 50 may then be separated from each other. The distal end 40*b* of the sheath 40 is proximal of the sheath 50 distal end 50*b*, since the stepped down section 52 prevents the sheath 40 from extending further distal (in this example, therefore, the sheath 50 has a minimum length of L30 plus the added length for stepped down section 52 to ensure the sheath 50 covers the entire length of the scaffold/balloon 10/12). The health professional, after removing the clamp 42, grips the stepped down section 52 (only) and pulls it distally to remove the sheath 50 from the scaffold 10. In doing so the sheath 40 will naturally remove itself as well from the scaffold 10 since the two sheaths are connected via half 49. After the sheath 50 has been sufficiently withdrawn from the scaffold 10, the halves 48, 49 will naturally open up. As the sheath 50 continues to be pulled distally the connected half 49 pulls the sheath 40 from the scaffold. Since the halves 48, 49 easily deflect away from the scaffold at this point, there is minimal disruption to the scaffold-balloon 10/12 structural integrity.

As with the embodiments discussed in connection with FIGS. 1-2, one-piece sheaths may provide an intuitive removal for a health profession. By providing an extension for sheath 50 and connecting the sheaths 40, 50 it can be communicated fairly easily the steps involved for safely removing both sheaths. First, a holding clamp is removed. Second, the extension of the constraining sheath is gripped and pulled away from the distal end of the catheter assembly. This single motion can safely remove both sheaths since they are connected and the protecting sheath will not withdraw until the constraining sheath is substantially clear of the scaffold 10. This avoids or minimizes the potential that damaging shear forces will be applied to the surface of the scaffold/balloon 10/12 structure as the sheaths are being removed.

Inner surfaces of sheaths 30, 50 may have a relatively smooth surface typical of polymer tubes formed by a molding or extrusion process. FIGS. 7A-7C, 8A-8C and 9A-9B illustrate alternative embodiments of a constraining sheath (sheath 30') which may be used with either the one piece or two piece sheath embodiments described earlier. The inner surface 70 of the sheath 30' is formed to reduce friction between it and the protecting sheath, e.g., sheaths 20 or 40, respectively, when the sheath 30' is placed on, or removed from the scaffold-balloon 10/12. Sheath 30' therefore is designed so that it may be more easily slid over a protecting sheath without adversely affecting the desired preload provided by the same constraining sheath not having the altered inner surface; that is, a smooth surface. A constraining sheath with a non-smooth or non-cylindrical contacting surface may also be chosen as a way to increase the preload over a constraining sheath that does not have an altered surface, but without risking damage to the scaffold/balloon 10/12 when the constraining sheath is removed. Since the frictional forces resisting sliding are reduced by a non-smooth surface the preload applied to the scaffold may be higher, so that essentially the sliding resistance is the same (if the surface contact is reduced then the preload may be increased because frictional resistance to sliding is proportional to the product of the preload and surface-to-surface contact area).

By reducing frictional resistance to sliding motion when a constraining sheath is placed over, or removed from a scaffold 10, the scaffold/balloon 10/12 integrity can therefore be more reliably maintained. If frictional resistance to sliding motion of the constraining sheath relative to a protecting sheath is high enough to cause a constraining sheath to stick to a protecting sheath, then a shear force is applied to the surface of the scaffold 10, which can result in dislodgment of the scaffold 10 from the balloon 12 or damage to a coating on the scaffold 10. At the same time, as discussed previously, it is desirable to have a relatively high preload imposed by a constraining sheath to reduce recoil of the scaffold 10. The embodiments described below in connection with FIGS. 7A-7C, 8A-8C and 9A-9B help to satisfy both of these competing needs.

The description of embodiments of a reduced-friction constraining sheath 30' may refer to assemblies shown in, or described with reference to FIGS. 1 and 5. However, a friction-reducing and/or pre-load increasing (yet safely removable) constraining sheath according to the disclosure is not limited to these arrangements. In other embodiments a constraining sheath having a reduced friction inner surface may be applied to constrain a scaffold 10 recoil without a protecting sheath being used (the stiffness and preload of the constraining sheath, and/or sensitivity of the scaffold/balloon 10/12 structure to shearing forces is a factor to consider when deciding whether a protecting sheath is needed). It will be understood, therefore, that the embodiments discussed in connection with FIGS. 7A-7C, 8A-8C and 9A-9B may be practiced with or without a protecting sheath disposed between the constraining sheath and scaffold/balloon 10/12.

FIG. 7A depicts a front cross-sectional view of an alternative sheath pair to that described in connection with FIG. 1 or 5, respectively. For these embodiments, the constraining sheath (sheath 30') has formed on its inner surface 70 raised ridges 72 extending over the length of the sheath 30'. The raised ridges 72 contact the outer surface of the protecting sheath 20 while the sheath pair 20, 30' is positioned over the scaffold/balloon 10/12. By forming the ridges 72, there is less surface-to-surface contact between the constraining sheath 30' and protecting sheath 20. Hence, there is less frictional resistance when sliding the constraining sheath 30' over the protecting sheath 20. The surface-to-surface contact is reduced from the entire contacting inner and outer surfaces of the two sheaths to mostly the edges 72a of the ridges contacting the outer surface of the protecting sheath. The preload is thereby applied through the edge 72a contact with the outer surface. For a sufficient number of ridges 72 formed about the circumference of the inner surface 70 of the sheath 30', about the same preload can be applied to the scaffold 10 while reducing the frictional resistance to sliding motion between the constraining and protecting sheaths. The ridges may be formed from a mold for the outer sheath 30'/50' or extruded. FIG. 7B shows a side view of the sheath 30' according to this embodiment.

FIG. 7C shows an alternative construction for a sheath 30' having ridges to reduce friction. Here ridges 74 are formed using embedded wires 73 within the sheath 30' which are disposed near the inner surface 70. The wires run lengthwise over the sheath 30' to form similar ridges to ridges 72. The constraining sheath 30' of FIG. 7C may be formed by positioning the wires 73 within a mold forming the sheath 30', as is known in the art.

FIGS. 8A-8B depict other alternative embodiments for sheath 30'. According to these embodiments o-rings 76, circumferential ridges, or rings are formed over the inner surface 70, rather than length-wise ridges (FIGS. 7A-7B). The o-rings 76 may be formed by a mold as before and may use embedded wire rings (as was done for the sheath of FIG. 7C) to form the raised o-ring surfaces for contacting the outer surface of the protecting sheath.

Figure 9A:
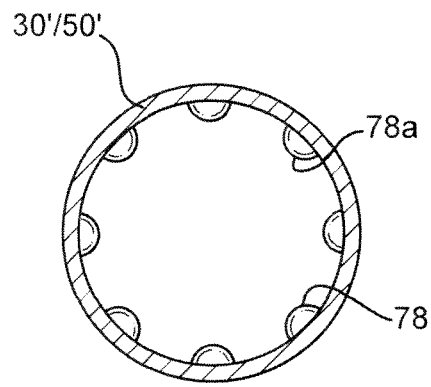
FIGS. 9A-9B show front and side views of a constraining sheath having an inner surface for reducing friction between the constraining sheath and a protecting sheath according to other alternative embodiments.
Figure 9B:
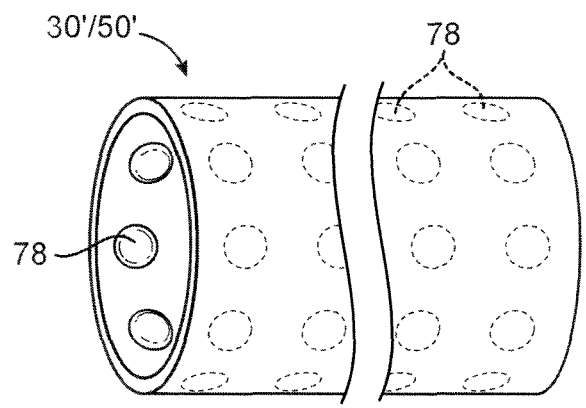

FIGS. 9A-9B illustrate another embodiment for sheath 30'/50'. According to this arrangement several nubs 78 are distributed over the inner surface 70 to form contacting surfaces 78a for applying the preload to the scaffold 10. As in the case of ridges 72, 74 or o-rings 76, the reduced surface-to-surface contact provided by the nubs 78 can reduce frictional resistance to sliding motion between the protecting and constraining sheaths without reducing the desired preload on the scaffold 10.

In alternative embodiments, the outer surface of the protecting sheath may include ridges, rings, nubs or a roughened surface, as opposed to the inner surface of the constraining sheath.

Figure 10A:
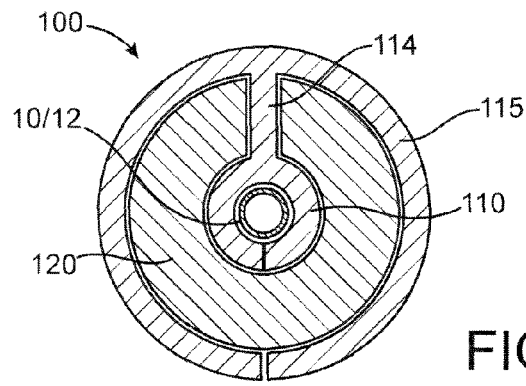
FIGS. 10A-10D depicts perspective and front views of a sheath assembly according to another embodiment.
Figure 10B:
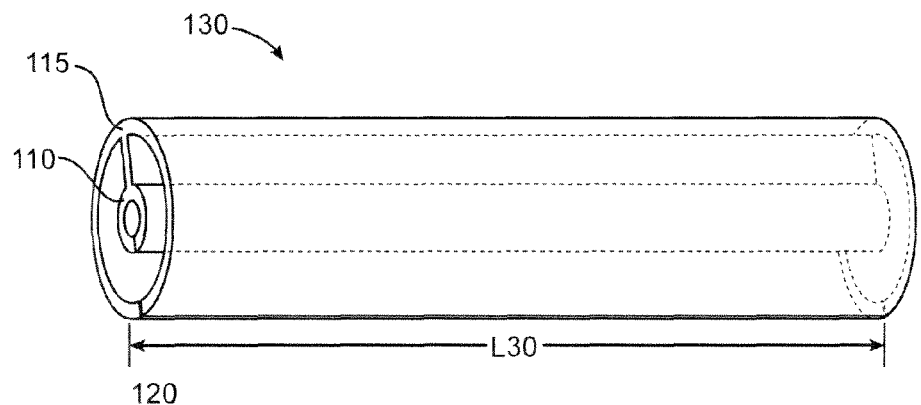
Figure 10C:
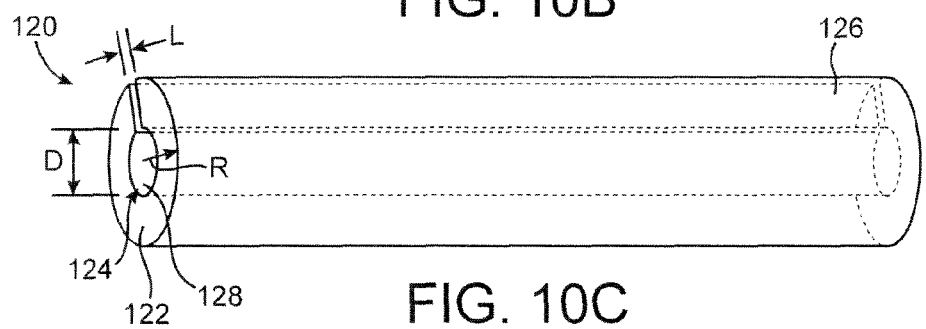
Figure 10D:
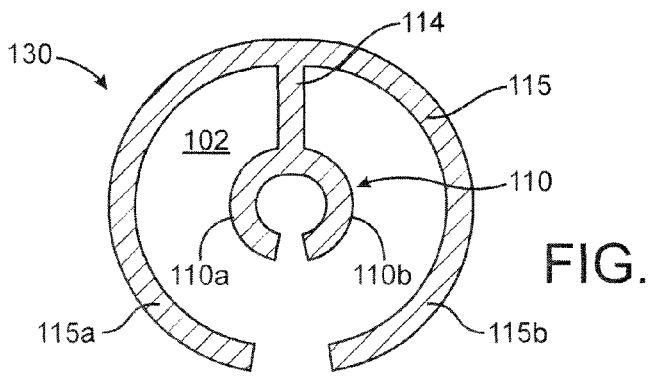

FIGS. 10A-10D illustrates aspects of a constraining and protecting sheath assembly according to other embodiments. Referring first to FIGS. 10B and 10D, the assembly includes a shell 130 forming an inner protecting 110 portion and outer handling 115 portion. Protecting portion 110 is connected to handling portion 115 by lengthwise extending link 114. FIG. 10B shows a perspective view of shell 130 and FIG. 10D a frontal view. Portions 110 and 115 are generally cylindrical in shape and have a length about equal to the length of sheath 30, i.e., length of L30. FIG. 10C shows a perspective view of a compression portion 120 having a shape sized to fit within the space 102 between the handling and protecting portions 115 and 110.

FIG. 10A shows an assembled view, which constrains recoil of a scaffold 10 using the assembled portions 110, 115 and piece 120. As depicted in this frontal view, the compression piece 120 is received in the space 102 to apply a compressive radial load on the protecting portion 110 to thereby apply the desired preload on the scaffold/balloon 10/12. The handling portion 115 is used to place the shell 130 on, and remove the shell 130 from the scaffold/balloon 10/12. The handling portion 115 provides a place for a medical professional to grip, or hold onto (so that the protecting portion 110 does not move relative to the scaffold 10) while the compression portion 120 is being removed. The handling portion 115 also acts to isolate the protection portion 110 from external forces.

Referring again to FIG. 10D, the protecting portion 110 is formed by half cylinder portions 110a, 110b which naturally deflect away, or spring apart from each other when the compression portion 120 is absent, as shown (compare to FIG. 10A). This facilitates safe removal of the shell 130 from, or placement of the shell 130 over the scaffold/balloon 10/12. Thus, when the compression portion 120 is removed a space formed between the half-cylinders 110a, 110b is increased such that the scaffold/balloon 10/12 can be easily inserted into or removed from the protecting portion 110 when the compression portion 120 is absent.

The handling portion 115 is also formed by two half cylinders 115a, 115b, but it may take on another shape while providing the same function. Also, the protecting portion 115 may be a single cylindrical piece, i.e., without a split. The handling portion 115 may also be constructed so that the half cylinders 115a, 115b deflect away from each other when the compression portion 120 is not received in the space 102 between the portions 110, 115. By having the half cylinders 115a, 115b spring apart like the half cylinders 110a, 110b, the compression portion 120 may be more easily inserted into, or removed from the space 102.

The compression portion 120 is sized to bring the half cylinders 110a, 110b together (thereby applying a preload on the scaffold 10) when compression portion 120 is pushed into the space 102. In a preferred embodiment, referring to FIG. 10C, the compression portion 120 has an outer radius that is smaller than the handling portion 115 and only contacts the protecting portion 110. For example, when the compression portion 120 is within the space 102 the handling portion 115 retains the same shape it had prior to inserting the compression portion 120. There is a gap between the compression portion 120 outer surface and the inner surface of the handling portion 115. As such, the handling portion 115 need not be used to provide or attain a desired preload. The compression portion 120/protecting portion 110 may fulfill this role, while the handling portion 115 is used handle the shell 130 when it is positioned over or removed from the scaffold 10, or to prevent inadvertent removal or sliding of the compression portion 120 over the protecting portion 110. In this embodiment the compression portion 120 is made from a stiffer material than 130. This allows the compression portion 120 to compress the half cylinders 110a and 110b without being significantly deformed itself. The compression portion 120 may be described as a cylindrical volume of the polymer material with a cut-out to form a key-hole like space 124 for receiving the link 114 and protecting portion 110 within the cylindrical volume.

In an alternate embodiment, the compression portion 120 is made from a relatively compressible polymer, compared to portions 115, 110. As before, the compression portion 120 may be described as a cylindrical volume of the flexible polymer material with a cut-out to form a key-hole like space 124 for receiving the link 114 and protecting portion 110 within the cylindrical volume. The compressive force is generated by the deformation of 120 between the handling portion 115 and the protecting portion 110. The material may be very soft, even foam or a composite soft material with a stiff core to ease insertion and removal. The low modulus of the material ensures that compressive force is relatively independent of the dimensions of the sheath or the scaffold.

The key-hole like space 124 forms a space with length L for receiving the link 114, and diameter D for receiving the protecting portion 110. The diameter D is such that the half cylinders 110a, 110b will be forcibly brought together when the half cylinders 110a, 110b are placed within the space 124. Thus, when the scaffold/balloon 10/12 is disposed between the half cylinders 110a, 110b and the protecting portion 110 inserted within the space 124, the half cylinders 110a, 110b can apply the desired preload on the scaffold 110 due to the inwardly directed radial compression forces caused by the compression portion 120. To facilitate placement of the compression portion 120 within the space 102, its outer surface 126 and inner surface 128 may be beveled along the proximal end. This will allow the compression portion 120 to slid along the handling portion 115 inner surface and protecting portion 110 outer surface as the compression portion 120 is being inserted into the space 102. When inserted into the space 102, the half cylinders 110a, 110b are forced together, so that the protecting portion 110 forms a cylinder enclosing the scaffold/balloon 10/12.

The compression portion 120 length is preferably longer than the length of shell 130, i.e., longer than length L30. This additional length allows a medical professional to easily grasp the compression portion 120 to remove it from the space 102. Preferably, this additional length would extend distal of the catheter distal end, similar to other embodiments, and may include a knob, raised or flared end that would function in a manner similar to the raised end 22 shown in FIG. 1.

In a method of assembly, the handling portion 115 is held while the distal end of the catheter assembly 2 is inserted between the half cylinders 110a, 110b. The compression portion 120 is then pushed into the space 102. This configures the assembly as shown in FIG. 10A. To remove the shell 130 from the catheter assembly 2, the compression portion 120 is first removed by pulling on the exposed portion of compression portion 120 while holding the handling portion 115. When removed in this manner, there are near zero shear forces acting on the scaffold 10. Removing compression portion 120, thereby cause the half cylinders 110a, 110b to deflect away from the scaffold! balloon 10/12 surface. The shell 130 may then be removed without causing damage to the scaffold/balloon 10/12.

Figure 11A:
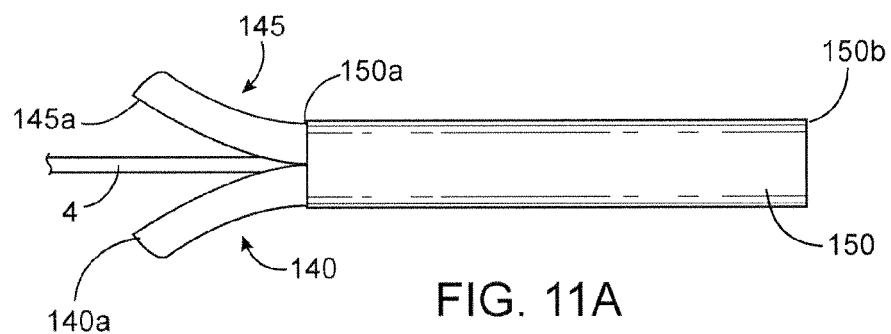
FIGS. 11A-11C shows a polymer scaffold-balloon catheter assembly with a pair of sheaths placed over the crimped scaffold, and removed from the scaffold according to another alternative embodiment.

FIGS. 11A-110 depicts a method of removing a sheath assembly from the scaffold/balloon 10/12 according to yet another embodiment. According to this embodiment, a protecting sheath has upper and lower halves 140, 145 of a cylinder, similar to upper and lowers cylindrical halves of sheath 20 or 40. However, unlike sheaths 20, 40 the halves 145, 140 are not connected to each other and extend sufficiently proximal of the scaffold 10 so that they may be gripped by a health professional and pulled radially outward to cause the constraining sheath 150 to be pushed off of the distal end of the catheter assembly. According to this embodiment, the constraining sheath 150 is removed by pulling radially outward on portions 145a, 140a, which portions may be regarded as a two-piece protecting sheath. Such an embodiment may be employed to assist with removal of a single sheath by disposing the halves 140, 145 over the scaffold/balloon 10/12 before the sheath 150 is placed.

Figure 11B:
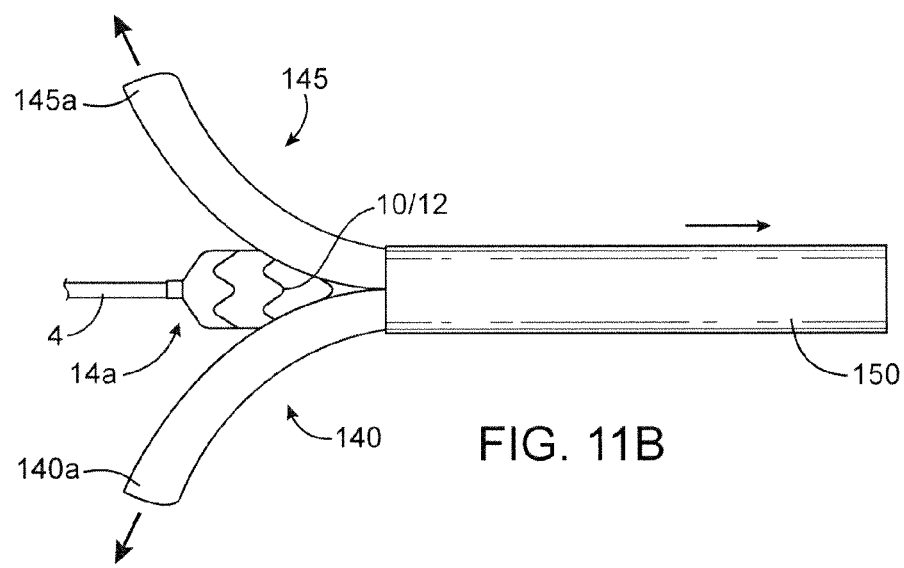
Figure 11C:
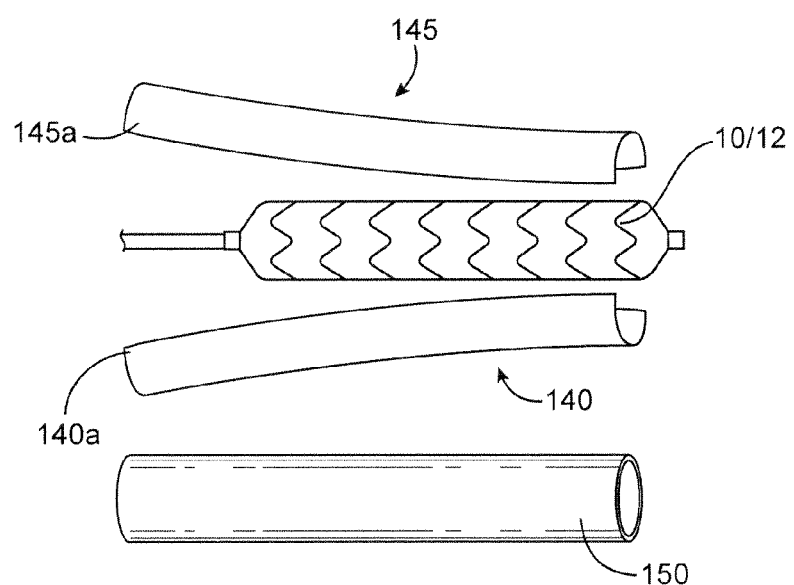

FIG. 11A shows a side view of a constraining sheath 150 over the scaffold/balloon 10/12. The protecting sheath has upper and lower halves 145, 140 which extend proximally of the scaffold 10. This is the arrangement of the packaged balloon-scaffold catheter assembly. To remove the sheaths, the health professional would grip the ends 145a, 140b of the protecting sheath and pull them radially apart from each other, as indicated in FIG. 11B. As the ends 145a and 140a are pulled outward, the constraining sheath 150 is stretched radially outward and pushed distally to cause it to fall off of the end of the catheter assembly 2, as shown in FIG. 11C.

Alternatively, the health professional may grip 150 and slide distally. Once 150 is no longer constraining, halves 140a and 145a will fall apart and release its constraint around the scaffold/catheter assembly 10/12.

Figure 12A:
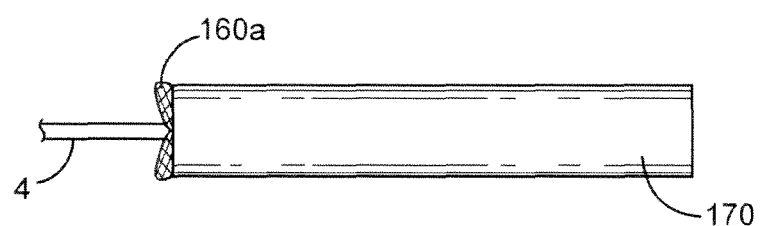
FIGS. 12A-12B shows a polymer scaffold-balloon catheter assembly with a sheath having an inner sleeve placed over the crimped scaffold, and removed from the scaffold according to another alternative embodiment.
Figure 12B:
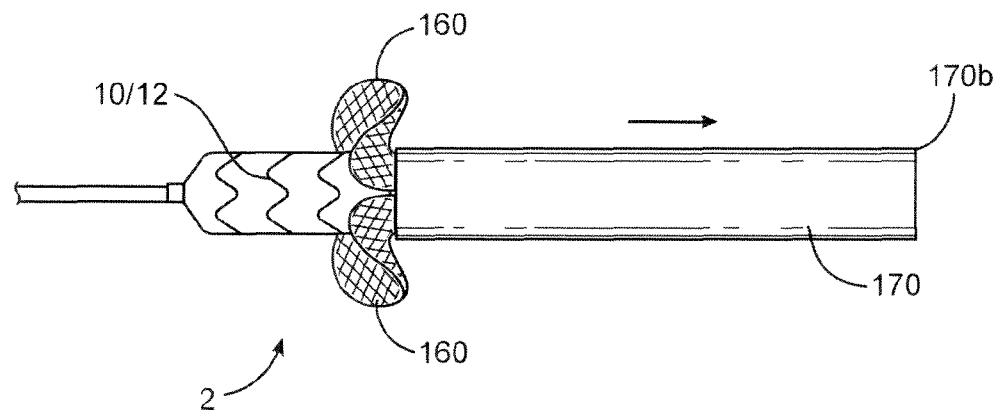

FIGS. 12A-12B depicts aspects of a one-piece sheath that both protects and constrains a scaffold/balloon 10/12 via a braided inner sleeve portion connected to the sheath. For this embodiment a constraining sheath 170 has an inner sleeve 160 attached to an inner surface of the constraining sheath 170. The inner sleeve 160 functions as a protecting sleeve portion of the sheath 170 to minimize shearing forces on the scaffold/balloon 10/12 as the constraining sheath 170 is removed from the scaffold/balloon 10/12. The inner sleeve 160 is formed as a braided wire sleeve. By forming the inner sleeve of braided wire, it will tend to roll outward proximally (as shown in FIG. 12B) as the constraining sheath 170 is pulled distally to remove it from the catheter assembly 2, rather than slide or dragged along with the constraining sheath portion 170 as it is pulled distally to remove the sheath 170 from the scaffold/balloon 10/12. In doing so, shearing forces on the scaffold 10 are minimized.

The braided wire sleeve 160 may be secured to the proximal end 170a of the constraining sheath 170 so that the sleeve 160 when removed from the sheath 170 is disposed proximally of the sheath 170. To assembly the device shown in FIG. 12A, the braided sleeve 160 is placed over the scaffold 10 so that the proximal end of the constraining sheath 170 is disposed distally over the scaffold 10. Then the sheath 170 is pushed over the braided wire sleeve 160.

As discussed earlier, a preferred crimping process includes a dwell period following the final crimp to reduce recoil of the scaffold when the crimping blades are removed. According to another embodiment of a constraining sheath a heat shrink process is utilized to affix a constraining sheath over a scaffold 10 to reduce recoil of the scaffold 10 after crimping. This heat shrink method of applying a constraining sheath may also reduce the dwell time needed to limit recoil of a scaffold 10 after crimping.

According to a method of crimping, a crimping process at or near to a glass transition temperature of the polymer of the scaffold 10 is conducted as explained in U.S. application Ser. No. 13/089,225 including FIGS. 1A and 1B and paragraphs [0042]-[0065]. Following crimping a radially stretched sheath is positioned over the scaffold 10 and heat applied to cause the sheath to heat shrink over the scaffold 10. In contrast to other embodiments, the heat shrunk sheath may provide not only a tight, constraining fit over the scaffold 10, but may also serve to reduce the scaffold/balloon 10/12 crossing profile down further due to the inherent inwardly directed compression forces caused by the heat shrunk tube.

Removal of a heat shrunk sheath may be facilitated by placing tabs, e.g., tabs or halves 145, 140 as in the embodiments of FIGS. 11A-11C, between the sheath and scaffold 10 surface before heat is applied to the stretched sheath. To remove the heat shrunk sheath from the scaffold 10, the half-cylinder tabs 145, 140 may be pulled radially outward, as explained earlier, to cause the heat shrunk sheath to be pushed off the distal end of the catheter assembly 2 without causing damaging to the scaffold/balloon 10/12.

In alternative embodiments, a sheath may be formed with slits or weakened areas that will facilitate a tearing away of the sheath when it is attached to a scaffold via a heat shrink. Examples of sheaths with slits or weakened areas for this purpose are described in U.S. application Ser. No. 12/916,349 including FIGS. 5A, 5B, 6A and 6B and paragraph nos. [0053]-[0055].

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the claims should not be construed to limit the invention to the specific embodiments disclosed in the specification. Rather, the scope of the invention is to be determined entirely by the claims, which are to be construed in accordance with established doctrines of claim interpretation.

What is claimed is:

1. An apparatus, comprising:
   a balloon catheter having a distal end and including a scaffold comprising a polymer crimped to a balloon of the catheter;
   a sheath disposed over the scaffold, the sheath applying a radial inward force on the crimped scaffold to limit recoil of the scaffold, the sheath comprising:
      a protecting portion having a distal end,
      a constraining portion having a distal end and being disposed over the protecting portion, wherein the constraining portion distal end is distal of the catheter distal end and the protecting portion distal end, and
      a connector portion connecting the protecting portion and constraining portion,
   wherein the protecting portion, constraining portion and connector portion comprise a unitary piece of flexible polymer material,
   wherein the connector portion is deformed into, or shaped as a loop having one end at the constraining portion and the other end at the protecting portion such that the distal end of the protecting portion may be received within a proximal end of the constraining portion, and
   wherein the apparatus is configured for being passed through the body of a patient only after the sheath is removed.

2. The apparatus of claim 1, wherein the constraining and protecting portions are configured so that the sheath is capable of being removed from the scaffold by the following steps:
   pulling an extension of the constraining portion distally to withdraw only the constraining portion from the scaffold and protecting portion,
   after the constraining portion has been displaced distally, continuing to pull the constraining portion distally to remove both the constraining portion and the protecting portion from the scaffold.

3. The apparatus of claim 1, wherein the protecting portion includes a first and second portion disposed over at least a substantial portion of the scaffold, the first and second portions configured for deflecting radially away from the scaffold when the constraining portion is removed from the scaffold.

4. The apparatus of claim 3, wherein the first portion is connected to a proximal end of the constraining portion.

5. The apparatus of claim 1, wherein the constraining portion includes a stepped down section.

6. An apparatus, comprising:
   a catheter assembly having a distal end and including a scaffold comprising a polymer crimped to a balloon;
   a sheath disposed over the scaffold, the sheath applying a radial inward force on the crimped scaffold to limit recoil of the scaffold, the sheath comprising:
      a protecting portion having a distal end,
      a constraining portion disposed over the protecting portion, the constraining portion including a stepped down section and a distal end that is distal of the catheter distal end and the protecting portion distal end, and
      a connector portion connecting the protecting portion and constraining portion,
   wherein the protecting portion, constraining portion and connector portion comprise a unitary piece of flexible polymer material,
   wherein the connector portion is deformed into, or shaped as a loop having one end at the constraining portion and the other end at the protecting portion such that the distal end of the protecting portion may be received within a proximal end of the constraining portion, and
   wherein the apparatus is configured for being passed through the body of a patient only after the sheath is removed by pulling the constraining portion away from the catheter distal end.

* * * * *